US006994991B1

(12) United States Patent
Duffy et al.

(10) Patent No.: US 6,994,991 B1
(45) Date of Patent: Feb. 7, 2006

(54) IDENTIFICATION OF DIFFERENTIALLY METHYLATED MULTIPLE DRUG RESISTANCE LOCI

(75) Inventors: Hao-Peng Xu Duffy, Centerport, NY (US); Ji-dong Shan, Flushing, NY (US); Li-ming Yuan, Flushing, NY (US); Daniel Budman, Locust Valley, NY (US); Anthony Calabro, Bethpage, NY (US)

(73) Assignee: North Shore - Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/441,857

(22) Filed: Nov. 18, 1999

Related U.S. Application Data

(60) Provisional application No. 60/108,994, filed on Nov. 18, 1998.

(51) Int. Cl.
*C12N 15/00* (2006.01)
*C12N 15/63* (2006.01)
*C12N 5/10* (2006.01)
*C07H 21/04* (2006.01)

(52) U.S. Cl. .............. 435/69.1; 435/320.1; 435/252.3; 435/254.11; 435/325; 530/23.5

(58) Field of Classification Search .............. 536/23.5; 514/12, 21; 530/324, 326–329, 23.5; 435/320.1, 435/69.1, 6, 252.3, 254.11, 325
See application file for complete search history.

(56) References Cited

U.S. PATENT DOCUMENTS

| 5,436,142 A | 7/1995 | Wigler |
| 5,489,519 A | 2/1996 | Deeley et al. |
| 5,552,277 A | 9/1996 | Nelson |
| 5,569,755 A | 10/1996 | Schweinfest |
| 5,766,880 A | 6/1998 | Deeley et al. |
| 5,786,146 A | 7/1998 | Herman et al. |
| 5,846,712 A | 12/1998 | Baylin |
| 5,856,094 A | 1/1999 | Sidransky |
| 5,871,917 A | 2/1999 | Duffy |

FOREIGN PATENT DOCUMENTS

| WO | WO 9746705 A1 | 12/1997 |
| WO | WO 9814615 A1 | 4/1998 |
| WO | WO 9854318 A1 | 12/1998 |
| WO | WO 9856952 A1 | 12/1998 |

OTHER PUBLICATIONS

Paul, W.E., ed., Fundamental Immunology (Textbook), 3rd edition, pp. 249-251, 1993.*
Klein, J. "Self-nonself discrimination, histoincompatability, and the concept of immunology" Immunogenetics, vol. 50, pp. 116-123, 1999.*
Ristori et al "Compostional bias and mimicry toward the nonself proteome in immunodominat T cell epitopes of sel and nonself" FASEB Journal, vol. 14, pp. 431-438, 2000.*
Seaver, Genetic and Engineering News, 1994, vol. 14, No. 14, pp. 10 and 21.*
Reiger et al, 1991, pp. 16-17.*
Bork and Koonin (Nature Genetics, 1998, vol. 18, pp. 313-318.*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-10.*
Orkin et al state ("Report and Recommendation of the Panel to Assess the NIH Investment in Research on Gene Therapy", NIH, 1995).*
Clark, S.J., Harrison, J. and Frommer, M. (1995) CpNpG methylation in mammalian cells. Nat. Genet. 10:20-27.
Gonzalgo, M.L., Liang, G., Spruck, C.H. 3rd, Zingg, J.M., Rideout, W.M. 3rd and Jones, P.A. (1997) Identification and characterization of differentially methylated regions of genomic DNA by methylation-sensitive arbitrarily primed PCR. Cancer Res. 57:594-599.
Herman, J.G., Graff, J.R., Myohanen, S., Nelkin, B.D. and Baylin, S.B. (1996) Methylation-specific PCR: a novel PCR assay for methylation status of CpG islands. Proc. Natl. Acad. Sci. U.S.A. 93:9821-9826.
Huang, T.H., Laux, D.E., Hamlin, B.C., Tran, P., Tran, H., Lubahn, D.B. (1997) Identification of DNA methylation markers for human breast carcinomas using the methylation-sensitive restriction fingerprinting technique. Cancer Res. 57:1030-1034.
Hubank, M. and Schatz, D.G. (1994) Identifying differences in mRNA expression by representational difference analysis of cDNA. Nucleic Acids Res. 22:5640-5648.
Kim, H., Barroso, M., Samanta, R., Greenberger, L. and Sztul, E. (1997) Experimentally induced changes in the endocytic traffic of P-glycoprotein alter drug resistance of cancer cells. Am. J. Physiol. 273(2 Pt 1):C687-702.

(Continued)

*Primary Examiner*—Karen A. Canella
(74) *Attorney, Agent, or Firm*—Kenyon & Kenyon

(57) ABSTRACT

The present invention provides genomic loci which are hypermethylated and differentially expressed in drug resistant cells compared to non-drug resistant cells. These genomic loci are homologous to the rab6 locus but map to a different chromosomal position. The present invention also provides nucleic acids isolated from these genomic loci by Methyl-Differential Display (MDD) methods, including genomic DNAs and cDNAs. The present nucleic acids are useful as probes for detecting mutations and the methylation patterns of the newly identified genomic loci, and of homologous nucleic acids. Nucleic acids of the present invention are also useful for detecting expression of mRNA from herein identified genes, for measuring expression of those and homologous genes sequences, and for determining suitability of therapeutic treatment. The disclosed nucleic acids and their homologs are useful for inhibition of multiple drug resistance. Cells are disclosed which are useful for identification or modulators of multidrug resistance.

9 Claims, 12 Drawing Sheets

OTHER PUBLICATIONS

Figure 5:
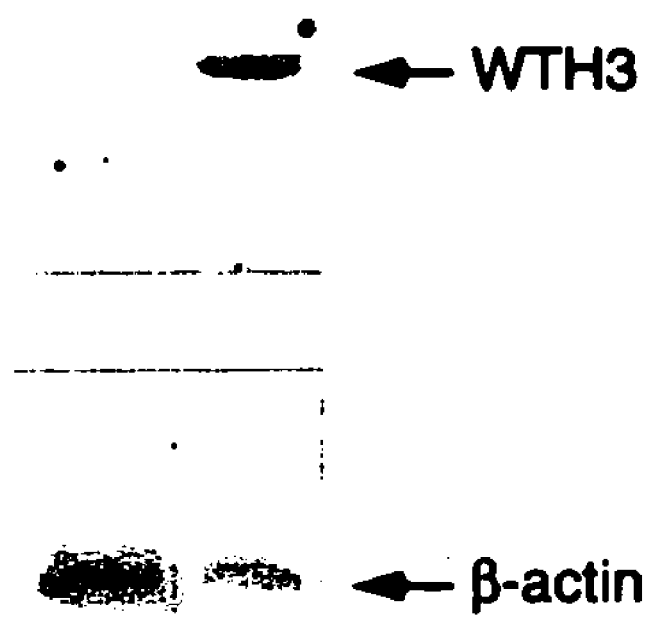

Lisitsyn, N., Lisitsyn, N. and Wigler, M. (1993) Cloning the differences between two complex genomes. Science 259: 946-951.

Martinez, O., Schmidt, A., Salamero, J., Hoflack, B., Roa, M. and Goud, B. (1994) The small GTP-binding protein rab6 functions in intra-Golgi transport. J. Cell Biol. 127: 1575-1588.

Martinez, O., Antony, C., Pehau-Arnaudet, G., Berger, E.G., Salamero, J. and Goud, B. (1997) GTP-bound forms of rab6 induce the redistribution of Golgi proteins into the endoplasmic reticulum. Proc. Natl. Acad. Sci. U.S.A. 94: 1828-1833.

Wieland, I., Bolger, G., Asouline, G. and Wigler, M. (1990) A method for difference cloning: gene amplification following subtractive hybridization. Proc. Natl. Acad. Sci. U.S.A. 87:2720-2724.

Zahraoui, A., Touchot, N., Chardin, P. and Tavitian, A. (1989) The human Rab genes encode a family of GTP-binding proteins related to yeast YPT1 and SEC4 products involved in secretion. J. Biol. Chem. 264:12394-12401.

Chen, X., Zehnbauer, B., Gnirke, A., Kwok, P.Y. (1997) Fluorescence energy transfer detection as a homogeneous DNA diagnostic method. Proc. Natl. Acad. Sci. USA 94: 10756-10761.

Han, J.A., Park, S.C. (1999) Reduction of transglutaminase 2 expression is associated with an induction of drug sensitivity in the PC-14 human lung cancer cell line. J. Cancer Res. Clin. Oncol. 125:89-95.

Nakayama, M., Wada, M., Harada, T., Nagayama, J., Kusaba, H., Ohshima, K., Kozuru, M., Komatsu, H., Ueda, R., Kuwano, M. (1998) Hypomethylation status of CpG sites at the promoter region and overexpression of the human MDR1 gene in acute myeloid leukemias.

* cited by examiner

```
CCGGGA_GGTCTCTGGGCTGAGGCGGCGACAGCTCCTCTAGTTCCACCATGTCCGCGGGC      59
||||||  |||||||  |||||||||||| | |||||||||||||||  ||||||  |||||
CCGGGACGGTCTCTAGGCTGAGGCGGCGGCCGCTCCTCTAGTTCCACAATGTCCACGGGC      82

GGAGACTTCGGGAATCCGCTGAGGAAATTCAAGCTGGTGTTCCTGGGGGAGCAAAGCGTT     119
||||||||||||||||||||||||||||||||||||||||||||||||||||||||||||
GGAGACTTCGGGAATCCGCTGAGGAAATTCAAGCTGGTGTTCCTGGGGGAGCAAAGCGTT     142

GCAAAGACATCTTTGATCACCAGATTCAGGTATGACAGTTTTGACAACACCTATCAGGCA     179
| ||||||||||||||||||||||||||||| ||||||||||||||||||||||||||||
GGAAAGACATCTTTGATCACCAGATTCATGTATGACAGTTTTGACAACACCTATCAGGCA     202

ATAATTGGCATTGACTTTTATCAAAAACTATGTACTTGGAGGATGGAACAATCGGGCTT     239
| |||||||||||||||||||||||||||||||||||||||||||||| |||||  |  |
ACAATTGGCATTGACTTTTATCAAAAACTATGTACTTGGAGGATCGAACAGTACGATTG     262

CGGCTGTGGGATACGGCGGGTCAGGAACGTCTCCGTAGCCTCATTCCCAGGTACATCCGT     299
|  |  ||||| || || |||||| || ||  || | || | ||||| || |||||  |||
CAATTATGGACACAGCAGGTCAAGAGCGGTTCAGGAGCTTGATTCCTAGCTACATTCGT     322

GATTCTGCTGCAGCTGTAGTAGTTTACGATATCACAAATGTTAACTCATTCCAGCAAACT     359
|| || |||  || || || ||||||  |||||||||||||||||||||||||||||||||
GACTCCACTGTGGCAGTTGTTGTTTATGATATCACAAATGTTAACTCATTCCAGCAAACT     382
```

FIG.1a

```
ACAAAGTGGATTGATGATGTCAGAACAGAAAGAGGAAGTGATGTTATCATCACGCTAGTA     419
||||||||||||||||||||||||||||||||||||||||||||||||||| |||||||
ACAAAGTGGATTGATGATGTCAGAACAGAAAGAGGAAGTGATGTTATCATCATGCTAGTA     442

GGAAATAGAACAGATCTTGCTGACAAGAGGCAAGTGTCAGTTGAGGAGGGAGAGAGGAAA     479
||||||| |||||||||||||||||||||||||||||| |||||||||||||||||||||
GGAAATAAAACAGATCTTGCTGACAAGAGGCAAGTGTCAATTGAGGAGGGAGAGAGGAAA     502

GCCAAAGGGCTGAATGTTACGTTTATTGAAACTAGGGCAAAAACTGGATACAATGTAAAG     539
||||||| |||||||||| ||||||||||||||| |||||| ||||||||||||||||||
GCCAAAGAGCTGAATGTTATGTTTATTGAAACTAGTGCAAAAGCTGGATACAATGTAAAG     562

CAGCTCTTTCGACGTGTAGCAGCAGCTTTGCCGGGAATGGAAAGCACACAGGACGGAAGC     599
||||||||||||||||||||||||||||||||||||||||||||||||||||||| |||||
CAGCTCTTTCGACGTGTAGCAGCAGCTTTGCCGGGAATGGAAAGCACACAGGACAGAAGC     622

AGAGAAGACATGAGTGACATAAAACTGGAAAAGCCTCAGGAGCAAACAGTCAGCGAAGGG     659
|||||||| |||| ||||||||||||||||||||||||||||||| ||||||| |||||
AGAGAAGATATGATTGACATAAAACTGGAAAAGCCTCAGGAGCAACCAGTCAGTGAAGGA     682

GGTTGTTCCTGCTACTCTCCCATGTCATCTTCAACCCTTCCTCAGAAGCCCCCTTACTCT     719
|| ||||||||||| | |||| ||||||||||||||| ||| |||||||| | || || |
GGCTGTTCCTGCTAATGTCCCTAGTCATCTTCAACC_TTCTTCAGAAGCTCACT_GCTTT     740
```

FIG.1b

```
MSAGGDFGNPLRKFKLVFLGEQSVAKTSLITRFRYDSFDNTYQAIIGIDFLSKTMYLEDG    60
MS GGDFGNPLRKFKLVFLGEQSV KTSLITRF YDSFDNTYQA IGIDFLSKTMYLED
MSTGGDFGNPLRKFKLVFLGEQSVGKTSLITRFMYDSFDNTYQATIGIDFLSKTMYLEDR    60

TIGLRLWDTAGQERLRSLIPRYIRDSAAAVVVYDITNVNSFQQTTKWIDDVRTERGSDVI   120
T+ L+LWDTAGQER RSLIP YIRDS  AVVVYDITNVNSFQQTTKWIDDVRTERGSDVI
TVRLQLWDTAGQERFRSLIPSYIRDSTVAVVVYDITNVNSFQQTTKWIDDVRTERGSDVI   120

ITLVGNRTDLADKRQVSVEEGERKAKGLNVTFIETRAKTGYNVKQLFRRVAAALPGMEST   180
I LVGN+TDLADKRQVS+EEGERKAK LNV FIET AK GYNVKQLFRRVAAALPGMEST
IMLVGNKTDLADKRQVSIEEGERKAKELNVMFIETSAKAGYNVKQLFRRVAAALPGMEST   180

QDGSREDMSDIKLEKPQEQTVSEGGCSC   208
QD SREDM DIKLEKPQEQ VSEGGCSC
QDRSREDMIDIKLEKPQEQPVSEGGCSC   208
```

FIG. 2

```
AGCTGGCTGGAGCAGCATCGGTCCGGGA_GGTCTCTAGGCTGAGGCGGCGGCCGCTCCTC    409
||||||||||||||||||||||||||||| |||||||||||||||||||||||||||||
AGCTGGCTGGAGCAGCATCGGTCCGGGACGGTCTCTAGGCTGAGGCGGCGGCCGCTCCTC     60

TAGTTCCACAATGTCCACGGGCGGAGACTTCGGGAATCCGCTGAGGAAATTCAAGCTGGT    469
||||||||||||||||||||||||||||||||||||||||||||||||||||||||||||
TAGTTCCACAATGTCCACGGGCGGAGACTTCGGGAATCCGCTGAGGAAATTCAAGCTGGT    120

GTTCCTGGGGGAGCAAAGCGTTGGAAAGACATCTTTGATCACCAGATTCATGTATGACAG    529
||||||||||||||||||||||||||||||||||||||||||||||||||||||||||||
GTTCCTGGGGGAGCAAAGCGTTGGAAAGACATCTTTGATCACCAGATTCATGTATGACAG    180

TTTTGACAACACCTATCAGGCAACAATTGGCATTGACTTTTATCAAAAACTATGTACTT     589
||||||||||||||||||||||||||||||||||||||||||||||||||||||||||||
TTTTGACAACACCTATCAGGCAACAATTGGCATTGACTTTTATCAAAAACTATGTACTT     240

GGAGGATCGAACAATCAGGCTTCAGCTGTGGGATACTGCGGGTCAGGAACGTTTCCGTAG    649
||||||||||||  |    |  ||   |  |||||  ||  ||  ||||| || || ||| | ||
GGAGGATCGAACAGTACGATTGCAATTATGGACACAGCAGGTCAAGAGCGGTTCAGGAG    300

CCTCATTCCCAGTTACATCCGTGATTCTGCTGCAGCTGTAGTAGTTTACGATATCACAAA    709
| |  |||||  ||  |||||  |||||  ||    |||  ||  ||  ||||||  |||||||||||
CTTGATTCCTAGCTACATTCGTGACTCCACTGTGGCAGTTGTTGTTTATGATATCACAAA    360

TGTTAACTCATTCCAGCAAACTACAAAGTGGATTGATGATGTCAGAACAGAAAGAGGAAG    769
||||||||||||||||||||||||||||||||||||||||||||||||||||||||||||
TGTTAACTCATTCCAGCAAACTACAAAGTGGATTGATGATGTCAGAACAGAAAGAGGAAG    420
```

FIG. 3a

```
TGATGTTATCATCATGCTAGTAGGAAATAAAACAGATCTTGCTGACAAGAGGCAAGTGTC    829
||||||||||||||||||||||||||||||||||||||||||||||||||||||||||||
TGATGTTATCATCATGCTAGTAGGAAATAAAACAGATCTTGCTGACAAGAGGCAAGTGTC    480

AATTGAGGAGGGAGAGAGGAAAGCCAAAGAGCTGAATGTTATGTTTATTGAAACTAGTGC    889
||||||||||||||||||||||||||||||||||||||||||||||||||||||||||||
AATTGAGGAGGGAGAGAGGAAAGCCAAAGAGCTGAATGTTATGTTTATTGAAACTAGTGC    540

AAAAGCTGGATACAATGTAAAGCAGCTCTTTCGACGTGTAGCAGCAGCTTTGCCGGGAAT    949
||||||||||||||||||||||||||||||||||||||||||||||||||||||||||||
AAAAGCTGGATACAATGTAAAGCAGCTCTTTCGACGTGTAGCAGCAGCTTTGCCGGGAAT    600

GGAAAGCACACAGGACAGAAGCAGAGAAGATATGATTGACATAAAACTGGAAAAGCCTCA   1009
||||||||||||||||||||||||||||||||||||||||||||||||||||||||||||
GGAAAGCACACAGGACAGAAGCAGAGAAGATATGATTGACATAAAACTGGAAAAGCCTCA    660

GGAGCAACCAGTCAGTGAAGGAGGCTGTTCCTGCTAATCTCCCATGTCATCTTCAACCTT   1069
|||||||||||||||||||||||||||||||||||| ||||   ||||||||||||||||
GGAGCAACCAGTCAGTGAAGGAGGCTGTTCCTGCTAATGTCCCTAGTCATCTTCAACCTT    720

CTTCAGAAGCTCACTGCTTT 1089
||||||||||||||||||||
CTTCAGAAGCTCACTGCTTT  740
```

FIG. 3b

```
MSTGGDFGNPLRKFKLVFLGEQSVGKTSLITRFMYDSFDNTYQATIGIDFLSKTMYLEDR    60
MSTGGDFGNPLRKFKLVFLGEQSVGKTSLITRFMYDSFDNTYQATIGIDFLSKTMYLEDR
MSTGGDFGNPLRKFKLVFLGEQSVGKTSLITRFMYDSFDNTYQATIGIDFLSKTMYLEDR    60

TIRLQLWDTAGQERFRSLIPSYIRDSAAAVVVYDITNVNSFQQTTKWIDDVRTERGSDVI   120
T+RLQLWDTAGQERFRSLIPSYIRDS   AVVVYDITNVNSFQQTTKWIDDVRTERGSDVI
TVRLQLWDTAGQERFRSLIPSYIRDSTVAVVVYDITNVNSFQQTTKWIDDVRTERGSDVI   120

IMLVGNKTDLADKRQVSIEEGERKAKELNVMFIETSAKAGYNVKQLFRRVAAALPGMEST   180
IMLVGNKTDLADKRQVSIEEGERKAKELNVMFIETSAKAGYNVKQLFRRVAAALPGMEST
IMLVGNKTDLADKRQVSIEEGERKAKELNVMFIETSAKAGYNVKQLFRRVAAALPGMEST   180

QDRSREDMIDIKLEKPQEQPVSEGGCSC    208
QDRSREDMIDIKLEKPQEQPVSEGGCSC
QDRSREDMIDIKLEKPQEQPVSEGGCSC    208
```

FIG. 4

FIG. 6

SEQUENCE LISTING

<160> NUMBER OF SEQ ID NOS: 46

<210> SEQ ID NO 1
<211> LENGTH: 24
<212> TYPE: DNA
<213> ORGANISM: Artificial Sequence
<220> FEATURE:
<223> OTHER INFORMATION: Synthetic adapter

<400> SEQUENCE: 1
ctcgtcgtca ggtcagtgct tcac                                    24

<210> SEQ ID NO 2
<211> LENGTH: 12
<212> TYPE: DNA
<213> ORGANISM: Artificial Sequence
<220> FEATURE:
<223> OTHER INFORMATION: Synthetic adapter

<400> SEQUENCE: 2
cggtgaagca ct                                                 12

<210> SEQ ID NO 3
<211> LENGTH: 24
<212> TYPE: DNA
<213> ORGANISM: Artificial Sequence
<220> FEATURE:
<223> OTHER INFORMATION: Synthetic adapter

<400> SEQUENCE: 3
tagagccacg tagctgctgt agtc                                    24

<210> SEQ ID NO 4
<211> LENGTH: 12
<212> TYPE: DNA
<213> ORGANISM: Artificial Sequence
<220> FEATURE:
<223> OTHER INFORMATION: Synthetic adapter

<400> SEQUENCE: 4
cggactacag ca                                                 12

<210> SEQ ID NO 5
<211> LENGTH: 24
<212> TYPE: DNA
<213> ORGANISM: Artificial Sequence
<220> FEATURE:
<223> OTHER INFORMATION: Synthetic adapter

<400> SEQUENCE: 5
accgtggact ggataggttc agac                                          24

<210> SEQ ID NO 6
<211> LENGTH: 12
<212> TYPE: DNA
<213> ORGANISM: Artificial Sequence
<220> FEATURE:
<223> OTHER INFORMATION: Synthetic adapter

<400> SEQUENCE: 6
cggtctgaac ct                                                       12

<210> SEQ ID NO 7
<211> LENGTH: 573
<212> TYPE: DNA
<213> ORGANISM: Homo sapiens
<220> FEATURE:
<221> NAME/KEY: CDS
<222> LOCATION: 48..573

<400> SEQUENCE: 7
ccgggaggtc tctgggctga ggcggcgaca gctcctctag ttccacc atg tcc gcg     56
                                                    Met Ser Ala
                                                      1 ggc gga gac ttc ggg aat ccg ctg agg aaa ttc aag ctg gtg ttc ctg   104
Gly Gly Asp Phe Gly Asn Pro Leu Arg Lys Phe Lys Leu Val Phe Leu
        5                  10                  15 ggg gag caa agc gtt gca aag aca tct ttg atc acc aga ttc agg tat   152
Gly Glu Gln Ser Val Ala Lys Thr Ser Leu Ile Thr Arg Phe Arg Tyr
 20                  25                  30                  35 gac agt ttt gac aac acc tat cag gca ata att ggc att gac ttt tta   200
Asp Ser Phe Asp Asn Thr Tyr Gln Ala Ile Ile Gly Ile Asp Phe Leu
                 40                  45                  50 tca aaa act atg tac ttg gag gat gga aca atc ggg ctt cgg ctg tgg   248
Ser Lys Thr Met Tyr Leu Glu Asp Gly Thr Ile Gly Leu Arg Leu Trp
         55                  60                  65 gat acg gcg ggt cag gaa cgt ctc cgt agc ctc att ccc agg tac atc   296
Asp Thr Ala Gly Gln Glu Arg Leu Arg Ser Leu Ile Pro Arg Tyr Ile
     70                  75                  80 cgt gat tct gct gca gct gta gta gtt tac gat atc aca aat gtt aac   344
Arg Asp Ser Ala Ala Ala Val Val Val Tyr Asp Ile Thr Asn Val Asn
 85                  90                  95 tca ttc cag caa act aca aag tgg att gat gat gtc aga aca gaa aga   392
Ser Phe Gln Gln Thr Thr Lys Trp Ile Asp Asp Val Arg Thr Glu Arg
100                 105                 110                 115 gga agt gat gtt atc atc acg cta gta gga aat aga aca gat ctt gct   440
Gly Ser Asp Val Ile Ile Thr Leu Val Gly Asn Arg Thr Asp Leu Ala
                120                 125                 130 gac aag agg caa gtg tca gtt gag gag gga gag agg aaa gcc aaa ggg   488
Asp Lys Arg Gln Val Ser Val Glu Glu Gly Glu Arg Lys Ala Lys Gly
            135                 140                 145 ctg aat gtt acg ttt att gaa act agg gca aaa act gga tac aat gta   536
Leu Asn Val Thr Phe Ile Glu Thr Arg Ala Lys Thr Gly Tyr Asn Val
        150                 155                 160

-continued

```
aag cag ctc ttt cga cgt gta gca gca gct ttg ccg g                          573
Lys Gln Leu Phe Arg Arg Val Ala Ala Ala Leu Pro
    165                 170                 175
```

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8

```
tcctctagtt ccaccatgtc cac                                                   23
```

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9

```
cacagccgaa gcccgattg                                                        19
```

<210> SEQ ID NO 10
<211> LENGTH: 838
<212> TYPE: DNA
<213> ORGANISM: Homo sapiens
<220> FEATURE:
<221> NAME/KEY: CDS
<222> LOCATION: 48..809

<400> SEQUENCE: 10

```
ccgggaggtc tctgggctga ggcggcgaca gctcctctag ttccacc atg tcc gcg             56
                                                    Met Ser Ala
                                                      1 ggc gga gac ttc ggg aat ccg ctg agg aaa ttc aag ctg gtg ttc ctg            104
Gly Gly Asp Phe Gly Asn Pro Leu Arg Lys Phe Lys Leu Val Phe Leu
      5                  10                  15 ggg gag caa agc gtt gca aag aca tct ttg atc acc aga ttc agg tat            152
Gly Glu Gln Ser Val Ala Lys Thr Ser Leu Ile Thr Arg Phe Arg Tyr
 20                  25                  30                  35 gac agt ttt gac aac acc tat cag gca ata att ggc att gac ttt tta            200
Asp Ser Phe Asp Asn Thr Tyr Gln Ala Ile Ile Gly Ile Asp Phe Leu
                 40                  45                  50 tca aaa act atg tac ttg gag gat gga aca atc ggg ctt cgg ctg tgg            248
Ser Lys Thr Met Tyr Leu Glu Asp Gly Thr Ile Gly Leu Arg Leu Trp
             55                  60                  65 gat acg gcg ggt cag gaa cgt ctc cgt agc ctc att ccc agg tac atc            296
Asp Thr Ala Gly Gln Glu Arg Leu Arg Ser Leu Ile Pro Arg Tyr Ile
         70                  75                  80 cgt gat tct gct gca gct gta gta gtt tac gat atc aca aat gtt aac            344
Arg Asp Ser Ala Ala Ala Val Val Val Tyr Asp Ile Thr Asn Val Asn
     85                  90                  95 tca ttc cag caa act aca aag tgg att gat gat gtc aga aca gaa aga            392
Ser Phe Gln Gln Thr Thr Lys Trp Ile Asp Asp Val Arg Thr Glu Arg
100                 105                 110                 115 gga agt gat gtt atc atc acg cta gta gga aat aga aca gat ctt gct            440
Gly Ser Asp Val Ile Ile Thr Leu Val Gly Asn Arg Thr Asp Leu Ala
                 120                 125                 130 gac aag agg caa gtg tca gtt gag gag gga gag agg aaa gcc aaa ggg            488
Asp Lys Arg Gln Val Ser Val Glu Glu Gly Glu Arg Lys Ala Lys Gly
             135                 140                 145
```

```
ctg aat gtt acg ttt att gaa act agg gca aaa act gga tac aat gta      536
Leu Asn Val Thr Phe Ile Glu Thr Arg Ala Lys Thr Gly Tyr Asn Val
        150                 155                 160 aag cag ctc ttt cga cgt gta gca gca gct ttg ccg gga atg gaa agc      584
Lys Gln Leu Phe Arg Arg Val Ala Ala Ala Leu Pro Gly Met Glu Ser
165                 170                 175 aca cag gac gga agc aga gaa gac atg agt gac ata aaa ctg gaa aag      632
Thr Gln Asp Gly Ser Arg Glu Asp Met Ser Asp Ile Lys Leu Glu Lys
180                 185                 190                 195 cct cag gag caa aca gtc agc gaa ggg ggt tgt tcc tgc tac tct ccc      680
Pro Gln Glu Gln Thr Val Ser Glu Gly Gly Cys Ser Cys Tyr Ser Pro
                200                 205                 210 atg tca tct tca acc ctt cct cag aag ccc cct tac tct ttc att gac      728
Met Ser Ser Ser Thr Leu Pro Gln Lys Pro Pro Tyr Ser Phe Ile Asp
            215                 220                 225 tgc agt gtg aat att ggc ttg aac ctt ttc cct tca tta ata acg ttt      776
Cys Ser Val Asn Ile Gly Leu Asn Leu Phe Pro Ser Leu Ile Thr Phe
        230                 235                 240 tgc aat tca tca ttg ctg cct gtc tcg tgg aga tgatctatta gcttgacaag    829
Cys Asn Ser Ser Leu Leu Pro Val Ser Trp Arg
245                 250             254 cacaaaaaa                                                            838

<210> SEQ ID NO 11
<211> LENGTH: 762
<212> TYPE: DNA
<213> ORGANISM: Homo sapiens
<220> FEATURE:
<221> NAME/KEY: CDS
<222> LOCATION: 1..762

<400> SEQUENCE: 11 atg tcc gcg ggc gga gac ttc ggg aat ccg ctg agg aaa ttc aag ctg       48
Met Ser Ala Gly Gly Asp Phe Gly Asn Pro Leu Arg Lys Phe Lys Leu
 1               5                  10                  15 gtg ttc ctg ggg gag caa agc gtt gca aag aca tct ttg atc acc aga       96
Val Phe Leu Gly Glu Gln Ser Val Ala Lys Thr Ser Leu Ile Thr Arg
             20                  25                  30 ttc agg tat gac agt ttt gac aac acc tat cag gca ata att ggc att      144
Phe Arg Tyr Asp Ser Phe Asp Asn Thr Tyr Gln Ala Ile Ile Gly Ile
         35                  40                  45 gac ttt tta tca aaa act atg tac ttg gag gat gga aca atc ggg ctt      192
Asp Phe Leu Ser Lys Thr Met Tyr Leu Glu Asp Gly Thr Ile Gly Leu
 50                  55                  60 cgg ctg tgg gat acg gcg ggt cag gaa cgt ctc cgt agc ctc att ccc      240
Arg Leu Trp Asp Thr Ala Gly Gln Glu Arg Leu Arg Ser Leu Ile Pro
 65                  70                  75                  80 agg tac atc cgt gat tct gct gca gct gta gta gtt tac gat atc aca      288
Arg Tyr Ile Arg Asp Ser Ala Ala Ala Val Val Val Tyr Asp Ile Thr
                 85                  90                  95 aat gtt aac tca ttc cag caa act aca aag tgg att gat gat gtc aga      336
Asn Val Asn Ser Phe Gln Gln Thr Thr Lys Trp Ile Asp Asp Val Arg
            100                 105                 110 aca gaa aga gga agt gat gtt atc atc acg cta gta gga aat aga aca      384
Thr Glu Arg Gly Ser Asp Val Ile Ile Thr Leu Val Gly Asn Arg Thr
        115                 120                 125 gat ctt gct gac aag agg caa gtg tca gtt gag gag gga gag agg aaa      432
Asp Leu Ala Asp Lys Arg Gln Val Ser Val Glu Glu Gly Glu Arg Lys
    130                 135                 140 gcc aaa ggg ctg aat gtt acg ttt att gaa act agg gca aaa act gga      480
Ala Lys Gly Leu Asn Val Thr Phe Ile Glu Thr Arg Ala Lys Thr Gly
145                 150                 155                 160
```

```
                    145                 150                 155                 160
tac aat gta aag cag ctc ttt cga cgt gta gca gca gct ttg ccg gga       528
Tyr Asn Val Lys Gln Leu Phe Arg Arg Val Ala Ala Ala Leu Pro Gly
                    165                 170                 175 atg gaa agc aca cag gac gga agc aga gaa gac atg agt gac ata aaa       576
Met Glu Ser Thr Gln Asp Gly Ser Arg Glu Asp Met Ser Asp Ile Lys
                    180                 185                 190 ctg gaa aag cct cag gag caa aca gtc agc gaa ggg ggt tgt tcc tgc       624
Leu Glu Lys Pro Gln Glu Gln Thr Val Ser Glu Gly Gly Cys Ser Cys
                    195                 200                 205 tac tct ccc atg tca tct tca acc ctt cct cag aag ccc cct tac tct       672
Tyr Ser Pro Met Ser Ser Ser Thr Leu Pro Gln Lys Pro Pro Tyr Ser
                    210                 215                 220 ttc att gac tgc agt gtg aat att ggc ttg aac ctt ttc cct tca tta       720
Phe Ile Asp Cys Ser Val Asn Ile Gly Leu Asn Leu Phe Pro Ser Leu
225                 230                 235                 240 ata acg ttt tgc aat tca tca ttg ctg cct gtc tcg tgg aga               762
Ile Thr Phe Cys Asn Ser Ser Leu Leu Pro Val Ser Trp Arg
                    245                 250         254

<210> SEQ ID NO 12
<211> LENGTH: 254
<212> TYPE: PRT
<213> ORGANISM: Homo sapiens

<400> SEQUENCE: 12

Met Ser Ala Gly Gly Asp Phe Gly Asn Pro Leu Arg Lys Phe Lys Leu
1               5                   10                  15

Val Phe Leu Gly Glu Gln Ser Val Ala Lys Thr Ser Leu Ile Thr Arg
            20                  25                  30

Phe Arg Tyr Asp Ser Phe Asp Asn Thr Tyr Gln Ala Ile Ile Gly Ile
        35                  40                  45

Asp Phe Leu Ser Lys Thr Met Tyr Leu Glu Asp Gly Thr Ile Gly Leu
    50                  55                  60

Arg Leu Trp Asp Thr Ala Gly Gln Glu Arg Leu Arg Ser Leu Ile Pro
65                  70                  75                  80

Arg Tyr Ile Arg Asp Ser Ala Ala Val Val Tyr Asp Ile Thr
            85                  90                  95

Asn Val Asn Ser Phe Gln Gln Thr Thr Lys Trp Ile Asp Asp Val Arg
            100                 105                 110

Thr Glu Arg Gly Ser Asp Val Ile Ile Thr Leu Val Gly Asn Arg Thr
        115                 120                 125

Asp Leu Ala Asp Lys Arg Gln Val Ser Val Glu Glu Gly Glu Arg Lys
    130                 135                 140

Ala Lys Gly Leu Asn Val Thr Phe Ile Glu Thr Arg Ala Lys Thr Gly
145                 150                 155                 160

Tyr Asn Val Lys Gln Leu Phe Arg Arg Val Ala Ala Ala Leu Pro Gly
                    165                 170                 175

Met Glu Ser Thr Gln Asp Gly Ser Arg Glu Asp Met Ser Asp Ile Lys
                    180                 185                 190

Leu Glu Lys Pro Gln Glu Gln Thr Val Ser Glu Gly Gly Cys Ser Cys
                    195                 200                 205

Tyr Ser Pro Met Ser Ser Ser Thr Leu Pro Gln Lys Pro Pro Tyr Ser
                    210                 215                 220

Phe Ile Asp Cys Ser Val Asn Ile Gly Leu Asn Leu Phe Pro Ser Leu
225                 230                 235                 240
```

Ile Thr Phe Cys Asn Ser Ser Leu Leu Pro Val Ser Trp Arg
                245                 250                 254

<210> SEQ ID NO 13
<211> LENGTH: 18
<212> TYPE: DNA
<213> ORGANISM: Homo sapiens

<400> SEQUENCE: 13 gga aca atc ggg ctt cgg                                           18
Gly Thr Ile Gly Leu Arg
  1               5

<210> SEQ ID NO 14
<211> LENGTH: 21
<212> TYPE: DNA
<213> ORGANISM: Homo sapiens

<400> SEQUENCE: 14 ctc cgt agc ctc att ccc agg                                       21
Leu Arg Ser Leu Ile Pro Arg
  1               5

<210> SEQ ID NO 15
<211> LENGTH: 39
<212> TYPE: DNA
<213> ORGANISM: Homo sapiens

<400> SEQUENCE: 15 ggg ctg aat gtt acg ttt att gaa act agg gca aaa act               39
Gly Leu Asn Val Thr Phe Ile Glu Thr Arg Ala Lys Thr
  1               5                  10

<210> SEQ ID NO 16
<211> LENGTH: 21
<212> TYPE: DNA
<213> ORGANISM: Homo sapiens

<400> SEQUENCE: 16 gga agc aga gaa gac atg agt                                       21
Gly Ser Arg Glu Asp Met Ser
  1               5

<210> SEQ ID NO 17
<211> LENGTH: 15
<212> TYPE: DNA
<213> ORGANISM: Homo sapiens

<400> SEQUENCE: 17 gag caa aca gtc agc                                               15
Glu Gln Thr Val Ser
  1               5

<210> SEQ ID NO 18
<211> LENGTH: 138
<212> TYPE: DNA
<213> ORGANISM: Homo sapiens

<400> SEQUENCE: 18 tac tct ccc atg tca tct tca acc ctt cct cag aag ccc cct tac tct   48
Tyr Ser Pro Met Ser Ser Ser Thr Leu Pro Gln Lys Pro Pro Tyr Ser
  1               5                  10                  15 ttc att gac tgc agt gtg aat att ggc ttg aac ctt ttc cct tca tta   96
Phe Ile Asp Cys Ser Val Asn Ile Gly Leu Asn Leu Phe Pro Ser Leu
                 20                  25                  30

```
ata acg ttt tgc aat tca tca ttg ctg cct gtc tcg tgg aga      138
Ile Thr Phe Cys Asn Ser Ser Leu Leu Pro Val Ser Trp Arg
         35                  40                  45
```

<210> SEQ ID NO 19
<211> LENGTH: 6
<212> TYPE: PRT
<213> ORGANISM: Homo sapiens

<400> SEQUENCE: 19

```
Gly Thr Ile Gly Leu Arg
 1               5
```

<210> SEQ ID NO 20
<211> LENGTH: 7
<212> TYPE: PRT
<213> ORGANISM: Homo sapiens

<400> SEQUENCE: 20

```
Leu Arg Ser Leu Ile Pro Arg
 1               5
```

<210> SEQ ID NO 21
<211> LENGTH: 13
<212> TYPE: PRT
<213> ORGANISM: Homo sapiens

<400> SEQUENCE: 21

```
Gly Leu Asn Val Thr Phe Ile Glu Thr Arg Ala Lys Thr
 1               5                  10
```

<210> SEQ ID NO 22
<211> LENGTH: 7
<212> TYPE: PRT
<213> ORGANISM: Homo sapiens

<400> SEQUENCE: 22

```
Gly Ser Arg Glu Asp Met Ser
 1               5
```

<210> SEQ ID NO 23
<211> LENGTH: 5
<212> TYPE: PRT
<213> ORGANISM: Homo sapiens

<400> SEQUENCE: 23

```
Glu Gln Thr Val Ser
 1               5
```

<210> SEQ ID NO 24
<211> LENGTH: 46
<212> TYPE: PRT
<213> ORGANISM: Homo sapiens

<400> SEQUENCE: 24

```
Tyr Ser Pro Met Ser Ser Ser Thr Leu Pro Gln Lys Pro Tyr Ser
 1               5                  10                  15

Phe Ile Asp Cys Ser Val Asn Ile Gly Leu Asn Leu Phe Pro Ser Leu
             20                  25                  30

Ile Thr Phe Cys Asn Ser Ser Leu Leu Pro Val Ser Trp Arg
         35                  40                  45
```

<210> SEQ ID NO 25
<211> LENGTH: 1460

```
<212> TYPE: DNA
<213> ORGANISM: Homo sapiens
<220> FEATURE:
<221> NAME/KEY: CDS
<222> LOCATION: 420..1043
<220> FEATURE:
<223> OTHER INFORMATION: cDNA (composite of multiple cDNA clones)

<400> SEQUENCE: 25
gaattccggg cagctgtgga agctcaggcg ctgcgcgtga gaggtcccag atacgtctgc    60
ggttccggct ccgccaccct cagcttctct tccccaggtc tgggagccga gtgcggaagg   120
agggaacggc cctagctttg gaagccaga ggacaccct ggctcctgcc gacaccgccc     180
tccttccctt cccagccgcg ggcctcgctc ggtgctaggc tactctgccg ggaggcggcg   240
gcggctgcca gtctgtggag agtcctgctg ccctccagcc gggctcctcc accgggcctt   300 gcagggccg agagagctcg gtgcccgccc ttccgctcgc cttttcgtc agctggctgg     360 agcagcatcg gtccgggagg tctctaggct gaggcggcgg ccgctcctct agttccaca   419 atg tcc acg ggc gga gac ttc ggg aat ccg ctg agg aaa ttc aag ctg    467
Met Ser Thr Gly Gly Asp Phe Gly Asn Pro Leu Arg Lys Phe Lys Leu
  1               5                  10                  15 gtg ttc ctg ggg gag caa agc gtt gga aag aca tct ttg atc acc aga    515
Val Phe Leu Gly Glu Gln Ser Val Gly Lys Thr Ser Leu Ile Thr Arg
             20                  25                  30 ttc atg tat gac agt ttt gac aac acc tat cag gca aca att ggc att    563
Phe Met Tyr Asp Ser Phe Asp Asn Thr Tyr Gln Ala Thr Ile Gly Ile
         35                  40                  45 gac ttt tta tca aaa act atg tac ttg gag gat cga aca atc agg ctt    611
Asp Phe Leu Ser Lys Thr Met Tyr Leu Glu Asp Arg Thr Ile Arg Leu
 50                  55                  60 cag ctg tgg gat act gcg ggt cag gaa cgt ttc cgt agc ctc att ccc    659
Gln Leu Trp Asp Thr Ala Gly Gln Glu Arg Phe Arg Ser Leu Ile Pro
 65                  70                  75                  80 agt tac atc cgt gat tct gct gca gct gta gta gtt tac gat atc aca    707
Ser Tyr Ile Arg Asp Ser Ala Ala Ala Val Val Val Tyr Asp Ile Thr
                 85                  90                  95 aat gtt aac tca ttc cag caa act aca aag tgg att gat gat gtc aga    755
Asn Val Asn Ser Phe Gln Gln Thr Thr Lys Trp Ile Asp Asp Val Arg
            100                 105                 110 aca gaa aga gga agt gat gtt atc atc atg cta gta gga aat aaa aca    803
Thr Glu Arg Gly Ser Asp Val Ile Ile Met Leu Val Gly Asn Lys Thr
        115                 120                 125 gat ctt gct gac aag agg caa gtg tca att gag gag gga gag agg aaa    851
Asp Leu Ala Asp Lys Arg Gln Val Ser Ile Glu Glu Gly Glu Arg Lys
130                 135                 140 gcc aaa gag ctg aat gtt atg ttt att gaa act agt gca aaa gct gga    899
Ala Lys Glu Leu Asn Val Met Phe Ile Glu Thr Ser Ala Lys Ala Gly
145                 150                 155                 160 tac aat gta aag cag ctc ttt cga cgt gta gca gca gct ttg ccg gga    947
Tyr Asn Val Lys Gln Leu Phe Arg Arg Val Ala Ala Ala Leu Pro Gly
                165                 170                 175 atg gaa agc aca cag gac aga agc aga gaa gat atg att gac ata aaa    995
Met Glu Ser Thr Gln Asp Arg Ser Arg Glu Asp Met Ile Asp Ile Lys
            180                 185                 190 ctg gaa aag cct cag gag caa cca gtc agt gaa gga ggc tgt tcc tgc   1043
Leu Glu Lys Pro Gln Glu Gln Pro Val Ser Glu Gly Gly Cys Ser Cys
        195                 200                 205 taatctccca tgtcatcttc aaccttcttc agaagctcac tgctttggcc ccttactct  1103 ttcattgact gcagtgtgaa tattggcttg aaccttttcc cttcagtaat aacgtattgc 1163
```

-continued

```
aattcatcat tgctgcctgt ctcgtggaga tgatctatta gcttcacaag cacaacaaaa    1223
gtcagtgtct tcattattta tattttacaa aaagccaaaa tatttcagca tattccagtg    1283
ataactttaa aaattagata cattttctta acatttttttt cttttttaat gttatgataa   1343
tgtacttcaa aatgatggaa atctcaacag tatgagtatg gcttggttaa cgagcggtat    1403
gttcacagcc tactttatct ctccttgctt ttctcacctc tcacttaccc ggaattc       1460
```

<210> SEQ ID NO 26
<211> LENGTH: 624
<212> TYPE: DNA
<213> ORGANISM: Homo sapiens
<220> FEATURE:
<221> NAME/KEY: CDS
<222> LOCATION: 1..624
<220> FEATURE:
<223> OTHER INFORMATION: coding region of cDNA

<400> SEQUENCE: 26

```
atg tcc acg ggc gga gac ttc ggg aat ccg ctg agg aaa ttc aag ctg        48
Met Ser Thr Gly Gly Asp Phe Gly Asn Pro Leu Arg Lys Phe Lys Leu
 1               5                  10                  15 gtg ttc ctg ggg gag caa agc gtt gga aag aca tct ttg atc acc aga        96
Val Phe Leu Gly Glu Gln Ser Val Gly Lys Thr Ser Leu Ile Thr Arg
             20                  25                  30 ttc atg tat gac agt ttt gac aac acc tat cag gca aca att ggc att       144
Phe Met Tyr Asp Ser Phe Asp Asn Thr Tyr Gln Ala Thr Ile Gly Ile
         35                  40                  45 gac ttt tta tca aaa act atg tac ttg gag gat cga aca atc agg ctt       192
Asp Phe Leu Ser Lys Thr Met Tyr Leu Glu Asp Arg Thr Ile Arg Leu
     50                  55                  60 cag ctg tgg gat act gcg ggt cag gaa cgt ttc cgt agc ctc att ccc       240
Gln Leu Trp Asp Thr Ala Gly Gln Glu Arg Phe Arg Ser Leu Ile Pro
 65                  70                  75                  80 agt tac atc cgt gat tct gct gca gct gta gta gtt tac gat atc aca       288
Ser Tyr Ile Arg Asp Ser Ala Ala Ala Val Val Val Tyr Asp Ile Thr
                 85                  90                  95 aat gtt aac tca ttc cag caa act aca aag tgg att gat gat gtc aga       336
Asn Val Asn Ser Phe Gln Gln Thr Thr Lys Trp Ile Asp Asp Val Arg
            100                 105                 110 aca gaa aga gga agt gat gtt atc atc atg cta gta gga aat aaa aca       384
Thr Glu Arg Gly Ser Asp Val Ile Ile Met Leu Val Gly Asn Lys Thr
        115                 120                 125 gat ctt gct gac aag agg caa gtg tca att gag gag gga gag agg aaa       432
Asp Leu Ala Asp Lys Arg Gln Val Ser Ile Glu Glu Gly Glu Arg Lys
    130                 135                 140 gcc aaa gag ctg aat gtt atg ttt att gaa act agt gca aaa gct gga       480
Ala Lys Glu Leu Asn Val Met Phe Ile Glu Thr Ser Ala Lys Ala Gly
145                 150                 155                 160 tac aat gta aag cag ctc ttt cga cgt gta gca gca gct ttg ccg gga       528
Tyr Asn Val Lys Gln Leu Phe Arg Arg Val Ala Ala Ala Leu Pro Gly
                165                 170                 175 atg gaa agc aca cag gac aga agc aga gaa gat atg att gac ata aaa       576
Met Glu Ser Thr Gln Asp Arg Ser Arg Glu Asp Met Ile Asp Ile Lys
            180                 185                 190 ctg gaa aag cct cag gag caa cca gtc agt gaa gga ggc tgt tcc tgc       624
Leu Glu Lys Pro Gln Glu Gln Pro Val Ser Glu Gly Gly Cys Ser Cys
        195                 200                 205
```

<210> SEQ ID NO 27
<211> LENGTH: 208

<212> TYPE: PRT
<213> ORGANISM: Homo sapiens

<400> SEQUENCE: 27

Met Ser Thr Gly Gly Asp Phe Gly Asn Pro Leu Arg Lys Phe Lys Leu
1               5                   10                  15

Val Phe Leu Gly Glu Gln Ser Val Gly Lys Thr Ser Leu Ile Thr Arg
            20                  25                  30

Phe Met Tyr Asp Ser Phe Asp Asn Thr Tyr Gln Ala Thr Ile Gly Ile
        35                  40                  45

Asp Phe Leu Ser Lys Thr Met Tyr Leu Glu Asp Arg Thr Ile Arg Leu
    50                  55                  60

Gln Leu Trp Asp Thr Ala Gly Gln Glu Arg Phe Arg Ser Leu Ile Pro
65                  70                  75                  80

Ser Tyr Ile Arg Asp Ser Ala Ala Val Val Tyr Asp Ile Thr
                85                  90                  95

Asn Val Asn Ser Phe Gln Gln Thr Thr Lys Trp Ile Asp Asp Val Arg
            100                 105                 110

Thr Glu Arg Gly Ser Asp Val Ile Ile Met Leu Val Gly Asn Lys Thr
        115                 120                 125

Asp Leu Ala Asp Lys Arg Gln Val Ser Ile Glu Glu Gly Glu Arg Lys
    130                 135                 140

Ala Lys Glu Leu Asn Val Met Phe Ile Glu Thr Ser Ala Lys Ala Gly
145                 150                 155                 160

Tyr Asn Val Lys Gln Leu Phe Arg Arg Val Ala Ala Ala Leu Pro Gly
                165                 170                 175

Met Glu Ser Thr Gln Asp Arg Ser Arg Glu Asp Met Ile Asp Ile Lys
            180                 185                 190

Leu Glu Lys Pro Gln Glu Gln Pro Val Ser Glu Gly Cys Ser Cys
        195                 200                 205

<210> SEQ ID NO 28
<211> LENGTH: 23
<212> TYPE: DNA
<213> ORGANISM: Artificial Sequence
<220> FEATURE:
<223> OTHER INFORMATION: Synthetic primer

<400> SEQUENCE: 28
tcctctagtt ccaccatgtc cgc                                    23

<210> SEQ ID NO 29
<211> LENGTH: 17
<212> TYPE: DNA
<213> ORGANISM: Artificial Sequence
<220> FEATURE:
<223> OTHER INFORMATION: Synthetic primer

<400> SEQUENCE: 29
gtaaaacgac ggccagt                                           17

<210> SEQ ID NO 30
<211> LENGTH: 24
<212> TYPE: DNA
<213> ORGANISM: Artificial Sequence
<220> FEATURE:
<223> OTHER INFORMATION: Synthetic primer

<400> SEQUENCE: 30
agcggataac aatttcacac agga                                   24

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
tcctctagtt ccacaatgtc c                                         21

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
gcaatcgtac tgttcgatc                                            19

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
cggagtcaac ggatttggtc gtat                                      24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
agccttctcc atggtggtga agac                                      24

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
gctgaggaaa ttcaagctgg                                           20

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
caacaactgc cacagtggag tc                                        22

<210> SEQ ID NO 37
<211> LENGTH: 22
<212> TYPE: DNA
<213> ORGANISM: Artificial Sequence
<220> FEATURE:

```
<223> OTHER INFORMATION: Synthetic primer

<400> SEQUENCE: 37
ctactacagc tgcagcagaa tc                                              22

<210> SEQ ID NO 38
<211> LENGTH: 21
<212> TYPE: DNA
<213> ORGANISM: Artificial Sequence
<220> FEATURE:
<223> OTHER INFORMATION: Synthetic primer

<400> SEQUENCE: 38
acgacatgga gaagatctgg c                                               21

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
ttctcgatgc tcgacgggct acc                                             23

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
gatggaacaa tcgggcttcg                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
aaacagtcag cgaagggggt                                                 20

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
gtagcaggaa caacccccctt cg                                             22

<210> SEQ ID NO 43
<211> LENGTH: 21
<212> TYPE: DNA
<213> ORGANISM: Artificial Sequence
<220> FEATURE:
<223> OTHER INFORMATION: Synthetic primer

<400> SEQUENCE: 43
gatcgaacaa tcaggcttca g                                               21
```

```
<210> SEQ ID NO 44
<211> LENGTH: 21
<212> TYPE: DNA
<213> ORGANISM: Artificial Sequence
<220> FEATURE:
<223> OTHER INFORMATION: Synthetic primer

<400> SEQUENCE: 44 aaggggggcca aagcagtgag c                                        21

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ggatcgaaca gtacgattgc                                           20

<210> SEQ ID NO 46
<211> LENGTH: 23
<212> TYPE: DNA
<213> ORGANISM: Artificial Sequence
<220> FEATURE:
<223> OTHER INFORMATION: Synthetic primer

<400> SEQUENCE: 46
gctgctgcta cacgtcgaaa gag                                       23
```

IDENTIFICATION OF DIFFERENTIALLY METHYLATED MULTIPLE DRUG RESISTANCE LOCI

RELATED U.S. APPLICATIONS

The present application claims the benefit under 35 U.S.C. § 119(e) of U.S. Provisional Application No. 60/108,994, filed Nov. 18, 1998. The disclosures of U.S. Ser. No. 08/657,866, filed May 31, 1996, U.S. Ser. No. 09/163,951, filed Sep. 30, 1998 and U.S. Ser. No. 09/345,881, filed Jun. 30, 1999 are hereby incorporated by reference.

FIELD OF THE INVENTION

The present invention provides nucleic acids isolated by Methyl- (or Mutant-) Differential Display (MDD) methods and methods for detecting mutations and/or the methylation patterns in multiple drug resistance loci. Genes are frequently not methylated in the cells where they are expressed but are methylated in cell types where they are not expressed. Moreover, tumor cell DNA is frequently methylated to a different extent and in different regions than is the DNA of normal cells. According to the present invention, the methylation pattern in a multiple drug resistance locus can, surprisingly, be altered and can give rise to altered expression patterns of that multiple drug resistance locus. Nucleic acids corresponding to the identified loci are useful as probes for detecting mutations and methylation patterns of the newly identified genomic loci, and of homologous nucleic acids. Nucleic acids of the present invention are also useful for detecting expression of mRNA from herein identified genes, for measuring expression of those and homologous genes sequences, and for determining suitability of therapeutic treatment. The disclosed nucleic acids and their homologs are useful for inhibition of multiple drug resistance. Cells are disclosed which are useful for identification or modulators of multidrug resistance.

BACKGROUND OF THE INVENTION

DNA is often methylated in normal mammalian cells. Patterns of DNA methylation have been found to correlate with patterns of gene expression. For example, differential methylation is found where maternal and paternal alleles of a gene in a zygote are differentially expressed. See Melissa Little et al., *Methylation and p16: Suppressing the Suppressor*, 1 NATURE MEDICINE 633 (1995). While methylation is known to occur at CpG sequences, only recent studies indicate that CpNpG sequences may be methylated. Susan J. Clark et al., *CpNpG Methylation in Mammalian Cells*, 10 NATURE GENETICS 20, 20 (1995). Methylation at CpG sites has been much more widely studied and is better understood.

Methylation of CpG sequences occurs by enzymatic recognition followed by placement of a methyl ($CH_3$) group on the fifth carbon atom of a cytosine base. The enzyme that mediates methylation of CpG dinucleotides, 5-cytosine methyltransferase, is essential for embryonic development—without it embryos die soon after gastrulation. It is not yet clear whether this enzyme methylates CpNpG sites. Peter W. Laird et al., *DNA Methylation and Cancer*, 3 HUMAN MOLECULAR GENETICS 1487, 1488 (1994).

When a gene has many methylated cytosines it is less likely to be expressed. K. Willson, 7 TRENDS GENET. 107–109 (1991). Hence, if a maternally-inherited gene is more highly methylated than the paternally-inherited gene, the paternally-inherited gene will generally give rise to more gene product. Similarly, when a gene is expressed in a tissue-specific manner, that gene will often be unmethylated in the tissues where it is active, but will be highly methylated in the tissues where it is inactive. Incorrect methylation is thought to be the cause of some diseases, including Beckwith-Wiedemann syndrome and Prader-Willi syndrome. I. Henry et al., 351 NATURE 665, 667 (1991); R. D. Nicholls et al., 342 NATURE 281, 281–85 (1989).

The methylation patterns of DNA from tumor cells are generally different than those of normal cells. Laird et al., supra. Tumor cell DNA is generally undermethylated relative to normal cell DNA, but selected regions of the tumor cell genome may be more highly methylated than the same regions of a normal cell genome. Hence, detection of altered methylation patterns in the DNA of a tissue sample is an indication that the tissue is cancerous. For example, the gene for Insulin-Like Growth Factor 2 (IGF2) is hypomethylated in a number of cancerous tissues, such as Wilm's Tumors, rhabdomyosarcoma, lung cancer and hepatoblastomas. Rainner et al. 362 NATURE 747–49 (1993); Ogawa, et al., 362 NATURE 749–51 (1993); S. Zhan et al., 94 J. CLIN. INVEST. 445–48 (1994); P. V. Pedone et al., 3 HUM. MOL. GENET. 1117–21 (1994); H. Suzuki et al., 7 NATURE GENET 432–38 (1994); S. Rainier et al., 55 CANCER RES. 1836–38 (1995).

The present invention is directed to nucleic acids which are differentially methylated in cells exhibiting multiple drug resistance relative to drug sensitive cells. Such nucleic acids, including nucleic acids specifically disclosed herein, are isolated by virtue of differential methylation at CpG dinucleotide or CpNpG trinucleotide sequences. Surprisingly, nucleic acids disclosed herein are homologous, but not identical, to members of a known gene family, particularly the RAB6 gene. We adhere to the nomenclature whereby human genes are designated with uppercase letters (e.g., WTH3, RAB6C, RAB6), and designate encoded proteins and peptides with lowercase letters (e.g., wth3, rab6c, rab6).

Multiple drug resistances (MDR) to a broad spectrum of chemotherapeutic agents is a major obstacle in the clinical treatment of human cancer. The most extensively studied proteins, mdr1 and mrp, are structurally similar to, and are members of, the ATP-binding cassette (ABC) transporter family. Previous studies provide no cytogenetic or molecular proof of gene amplifications which might explain an elevated expression of MDR1 or MRP genes. The present invention provides nucleic acids which are homologous to the RAB6 locus. Surprisingly, the present nucleic acids were isolated because they are hypermethylated in a drug resistance cell line. Moreover, rather than being over-expressed, the present nucleic acids appear to be underexpressed in multiple drug resistance cells.

SUMMARY OF THE INVENTION

The present invention provides an isolated nucleic acid encoding a human wth3 protein or an immunogenic fragment thereof. The nucleic acid can encode an amino acid sequence comprising SEQ ID NO:12 from about amino acid residue number 1 to about amino acid residue number 175. The nucleic acid can be SEQ ID NO:7 or SEQ ID NO:11. Alternatively, the nucleic acid can encode immunogenic fragments of wth3 which comprise amino acids of SEQ ID NO:19, or SEQ ID NO:20, or SEQ ID NO:21, or SEQ ID NO:22, or SEQ ID NO:23 or SEQ ID NO:24.

The present invention also provides an isolated nucleic acid encoding a human rab6c protein or an immunogenic fragment thereof. The nucleic acid can encode an amino acid sequence comprising SEQ ID NO:27 from about amino acid residue number 1 to about amino acid residue number 208. The nucleic acid can be SEQ ID NO:25 or SEQ ID NO:26.

The present invention is also directed to a recombinant DNA and an expression vector which includes any one of the present nucleic acids operably linked to regulatory control nucleic acid which effects expression of the nucleic acid in a host cell.

The present invention is further directed to a host cell which contains such a recombinant DNA or such an expression vector.

The present invention also contemplates a process for producing a recombinant wth3 protein or immunogenic fragment thereof, or a recombinant rab6c protein or immunogenic fragment thereof. The process involves: a) culturing a host cell which contains an expression vector having one of the present nucleic acids in a culture medium under conditions suitable for expression of one of said recombinant proteins in the host cell, and b) isolating the recombinant protein from the host cell or the culture medium.

The present invention further contemplates a substantially purified protein or polypeptide which comprises amino acids of SEQ ID NO:12 or SEQ ID NO:19 or SEQ ID NO:20 or SEQ ID NO:21 or SEQ ID NO:22 or SEQ ID NO:23 or SEQ ID NO:24. Alternatively, the substantially purified protein can include the amino acid sequence depicted in SEQ ID NO: 27 from about amino acid residue number 1 to about amino acid residue number 208.

The present invention is also directed to an isolated nucleic acid which includes a sequence of at least about 12 nucleotides, preferably at least about 15 nucleotides of SEQ ID NO:10 which is capable of hybridizing to a nucleic acid segment of a WTH3 gene under hybridization conditions wherein the nucleic acid fails to hybridize to a nucleic acid segment of a RAB6 gene. In one embodiment the hybridization conditions are stringent.

The present invention also provides an isolated nucleic acid which includes SEQ ID NO:10 from about nucleotide number 1 to about nucleotide number 838. In another embodiment such an isolated nucleic acid can have at least 20 adjacent nucleotides of SEQ ID NO:10; such a nucleic acid may have up to at least 100 adjacent nucleotides of SEQ ID NO:10.

The present invention further provides an antibody which binds to wth3 protein, wherein the affinity of such an antibody for the wth3 protein is greater than the affinity of the antibody for a rab6 protein. The wth3 protein can comprise the amino acid sequence of SEQ ID NO:12 from about amino acid residue number 1 to about amino acid residue number 254. In a preferred embodiment the antibody binds to wth3 and not to rab6. Methods of producing a hybridoma which secretes such an antibody are also provided. Such a method includes a) immunizing an animal with wth3 or a polypeptide fragment thereof; b) obtaining lymphoid cells from the immunized animal; c) fusing the lymphoid cells and an immortalizing cell to produce hybrid cells; and d) selecting hybrid cells which produce antibody that: i) specifically binds to wth3, and ii) does not bind to rab6.

The present invention further provides a method for identifying wth3 in a test sample, which includes a) contacting the test sample with an anti-wth3 antibody or fragment thereof that specifically binds to wth3 protein, such that wth3 protein binds to the anti-wth3 antibody and forms a complex therewith; b) contacting the complex with a reporter molecule which includes a signal generating compound capable of binding to the anti-wth3 antibody or fragment thereof; and c) detecting the signal generating compound, to thereby detect the wth3 protein. This method may also include an additional step where a control sample having substantially no wth3 protein is contacted with the anti-wth3 antibody or fragment thereof.

The present invention also provides a method for identifying wth3 protein in a test sample, which includes: a) contacting the test sample with a first anti-wth3 antibody that specifically binds to wth3 protein, such that wth3 protein binds to the first antibody and forms a complex therewith; b) contacting the complex formed in step (a) with a second antibody that specifically binds to wth3 protein so as to form a second complex which includes the first antibody, the wth3 protein, and the second antibody; c) contacting the second complex formed in step (b) with a reporter molecule that includes a signal generating compound wherein the reporter molecule is capable of binding to said first or second anti-wth3 antibody; and d) detecting the signal generating compound, thus detecting the wth3 protein. In a particular embodiment, either of the first or second anti-wth3 antibody is capable of being attached to a support. According to the present invention, either the first or the second anti-wth3 antibody has a greater affinity for wth3 protein than for rab6 protein. For example, the anti-wth3 antibody can have 1000-fold greater affinity for wth3 protein than for rab6 protein. In the preferred embodiment, the anti-wth3 antibody binds to wth3 protein and does not bind to rab6 protein. This method can also include a step for observing whether the first and the second antibody bind to a control sample having substantially no wth3 protein.

The present invention further involves a method for detecting whether a CG dinucleotide or a CNG trinucleotide is hypomethylated or hypermethylated in a genomic DNA homologous to WTH3 which is present in a test sample of cells. This method includes a) cleaving genomic DNA isolated from the test sample of cells with a master restriction enzyme to generate a cleaved test-cell DNA; b) hybridizing a probe to the cleaved test-cell DNA to form a hybridization complex; and c) determining the size of the hybridization complex; wherein the master restriction enzyme cleaves a nonmethylated CG or CNG DNA sequence but does not cleave a methylated CG or CNG DNA sequence, and wherein the probe is a nucleic acid which hybridizes to a WTH3 nucleic acid in the region of the CG or CNG sequence. The method may also include cleaving genomic DNA isolated from a control sample of cells, hybridizing a probe to the cleaved control-cell DNA to form a control-hybridization complex and determining whether the size of the control-hybridization complex is the same as the size of the test-hybridization complex. According to the present invention, the potentially methylated CG or CNG sequence is within 10 kb of the transcribed WTH3 sequence. The master restriction enzyme can be Hpa II.

By properly choosing the hybridization probe of step (b), the same method is useful for determining whether a CG dinucleotide or a CNG trinucleotide is hypomethylated or hypermethylated in the region of DNA which comprises RAB6.

The present invention also includes a method of identifying human WTH3 mRNA in a test sample which includes contacting a test sample with a nucleic acid probe that has a nucleotide sequence which is complementary to a portion of human WTH3 mRNA, and determining whether the probe hybridizes to an mRNA in the test sample. In another embodiment, this method involves an additional step of measuring the amount of WTH3 mRNA by measuring the amount of probe hybridized to the WTH3 mRNA. Measurements of WTH3 mRNA are made to determine whether the amount of WTH3 in a test sample is elevated or diminished. Amounts of WTH3 mRNA in different cells can be compared. For example, it is disclosed that the amount of WTH3 mRNA in multidrug resistant MCF7/AdrR cells is reduced compared to drug sensitive MCF7 cells. Alternatively, the amount of WTH3 mRNA in a particular cell is compared to the amount of one or more RNA species which are constitutively expressed. Two examples of such RNAs are those which encode β-actin and glyceraldehyde-3-phosphate dehydrogenase (GPDH).

In a preferred embodiment, the hybridization conditions prevent hybridization of the probe to an mRNA encoding a human rab6 protein but permit hybridization to an mRNA encoding a human wth3 protein. Preferred probes for detecting and measuring WTH3 mRNA contain nucleotide sequences which are specific to WTH3. However, probes which bind to any part of WTH3 may be useful. For example, a probe which hybridizes to both RAB6 and WTH3 can be used to measure RAB6 mRNA and WTH3 mRNA simultaneously. When comparing samples such as RNA from MCF7 and MCF7/AdrR cells, where both WTH3 and RAB6 mRNAs are differentially expressed in a similar fashion, it may not be necessary to differentiate between the two mRNA species. Of course, two such mRNA species may nevertheless be differentiated if necessary by some other characteristic. For example, it is possible to individually measure two homologous RNA species using a northern blot to separate them by size.

The present invention further provides a method for identifying human WTH3 mRNA in a test sample which includes nucleic acid amplification of an mRNA homologous to WTH3. This method may involve polymerase chain reaction (PCR) of an mRNA present the test sample using a first and a second PCR primer. For example, the method may involve annealing a first PCR primer to a test sample RNA, reverse transcribing an RNA homologous to WTH3 to provide a cDNA:RNA hybrid, melting the RNA:DNA hybrid to provide a single-stranded cDNA, annealing a second PCR primer onto the cDNA, primer-extending said second PCR primer to form a double stranded DNA, amplifying the double-stranded DNA using the first PCR primer and the second PCR primer to form an amplified double-stranded DNA, and detecting the amplified double-stranded DNA. In this example, the first PCR primer is complementary to a 3' portion of an WTH3 mRNA and may have SEQ ID NO:9, whereas the second PCR primer is complementary to the 3' end of the cDNA and may have SEQ ID NO:8 or SEQ ID NO:28.

The methods and nucleic acids of the present invention which are useful for determining expression of WTH3 are also useful for measuring expression of WTH3 and WTH3 homologs. For example, the present invention provides methods and nucleotides useful for measuring expression of RAB6C and RAB6. Using nucleotides of the present invention, it is shown that other mRNAs in addition to WTH3 are differentially expressed. The discovery of differential expression of WTH3 in normal and multiple drug resistant cells is extended to homologs of WTH3, including RAB6C and RAB6. Particular probes designed to measure expression of RAB6 also reveal expression of other homologous mRNAs of differing sizes. Similar to WTH3, it is observed that RAB6 and RAB6 homologs are differentially expressed in MCF7 and MCF7/AdrR drug resistant cells. The present invention contemplates kits and methods for the measurement of WTH3, RAB6 and their homologs, either individually or in combination.

By determining expression of WTH3, or RAB6C, or RAB6, or a homolog in a test sample from a cancer, the suitability of certain drugs for treatment of the cancer can be determined. For example, identification of a deficiency in expression in any of the aforementioned genes, would indicate discontinuation of and substitution for a therapeutic that is substantially ineffective for treatment of cells which have acquired multidrug resistance.

Nucleic acids of the present invention, when expressed in cells which otherwise exhibit MDR, are useful for inhibition of the drug resistant phenotype. The nucleic acids are shown to be useful for increasing drug sensitivity of MDR cells to doxorubicin. The present invention contemplates the use of nucleic acids homologous to RAB6 for the treatment of MDR cells and tumors.

Moreover, cells which overproduce wth3 or rab6c or rab6 or a homolog thereof are useful for identifying modulators or multidrug resistance.

BRIEF DESCRIPTIONS OF THE DRAWINGS

FIG. 1 provides a nucleotide sequence comparison of WTH3 (top) and RAB6 (bottom, GenBank Accession No. M28212) DNA sequences. The ATG start codons and the TAA termination codon of RAB6 are underlined. Nucleotide numbers correspond to GenBank Accession No. M28212 (RAB6) and SEQ ID NO:10 (WTH3).

FIG. 2 provides an amino acid sequence comparison of wth3 (top) and rab6 (bottom). Conservative substitutions are represented by "+".

FIG. 3 provides a comparison of RAB6C (top) and RAB6 (bottom) DNA sequences. The ATG start and TAA termination codons are underlined.

FIG. 4 provides an amino acid sequence comparison of rab6c (top) and rab6 (bottom). Conservative substitutions are represented by "+".

FIG. 5 depicts a Northern blot of mRNA from a non-drug resistant cell line, MCF7, and a drug resistant cell line, MCF7/AdrR, hybridized with a probe containing WTH3 sequences. The probe was prepared by amplification of a 573 bp WTH3 fragment which had been cloned into pUC118 (see Example 1). For quantitative comparison, the same mRNA was hybridized to a control probe which comprised a nucleotide sequence encoding a portion of β-actin, which is expressed in all tissues. As indicated by the density of the band, WTH3 transcripts are present at significantly higher levels in mRNA isolated from the non-drug resistant MCF7 cells (lane W) than in mRNA isolated from the drug resistant MCF/AdrR cells (lane A).

FIG. 6 depicts a northern blot of mRNA from non-drug resistant MCF7 cells (lane W) and drug resistant MCF7/AdrR cells (lane A) hybridized with a probe containing 208 bp of RAB6 sequence. For quantitative comparison, the same mRNA was hybridized with a control probe which comprised a nucleotide sequence encoding a portion of glyceraldehyde-3-phosphate dehydrogenase (GPDH). The RAB6 probe identified several bands, all of which appear with greater intensity in lane "W" relative to lane "A". The bands correspond to transcripts sizes ranging from 1.5 kb to over 4 kb.

Figure 7:
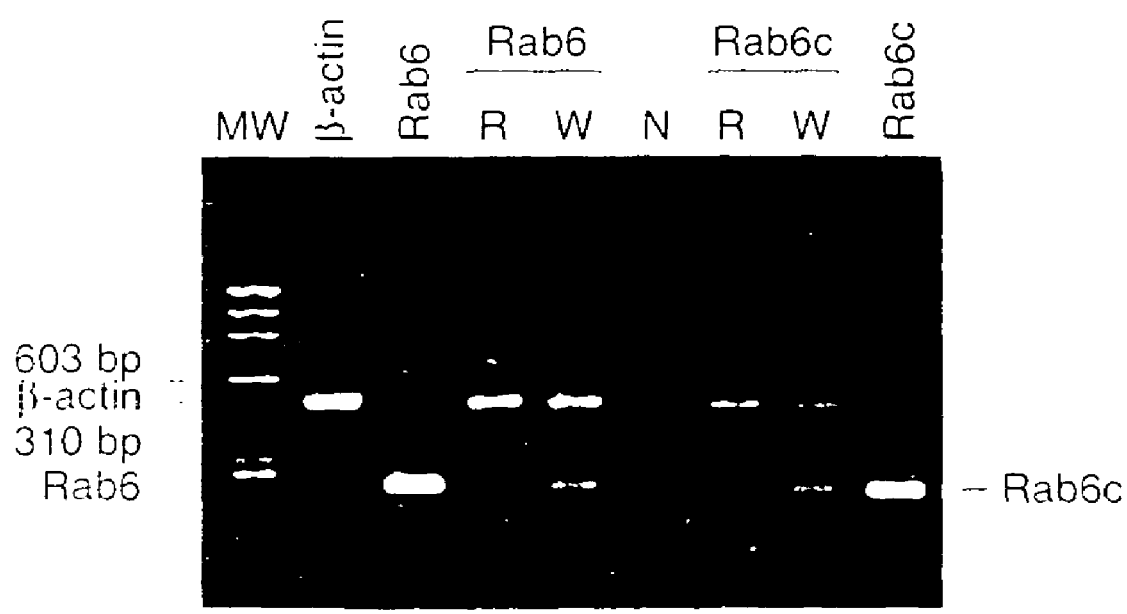

FIG. 7 depicts the results of a quantitative RT-PCR experiment for detecting amounts of RAB6 and WTH3/RAB6C transcripts in MCF7/AdrR cells (lanes labeled "R") and MCF7 cells (lanes labeled "W") genes. cDNA was synthesized from mRNA and amplified. β-actin served as a control as it is normally is expressed in all tissues. Amplification products for positive controls are shown in lanes labeled β-actin (495 bp), Rab6 (244 bp) and Rab6c (244 bp). For the R-W lane pair labeled Rab6, β-actin and RAB6 amplification products were generated in a single reaction using β-actin and RAB6 specific primers. The amount of RAB6 product is significantly reduced in MCF7/AdrR cells relative to MCF7 cells. For the R-W lane pair labeled Rab6c, β-actin and WTH3/RAB6C amplification products were generated in a single reaction using β-actin and WTH3/RAB6C specific primers. The amount of WTH3/RAB6c product is significantly reduced in MCF7/AdrR cells relative to MCF7 cells.

Figure 8:
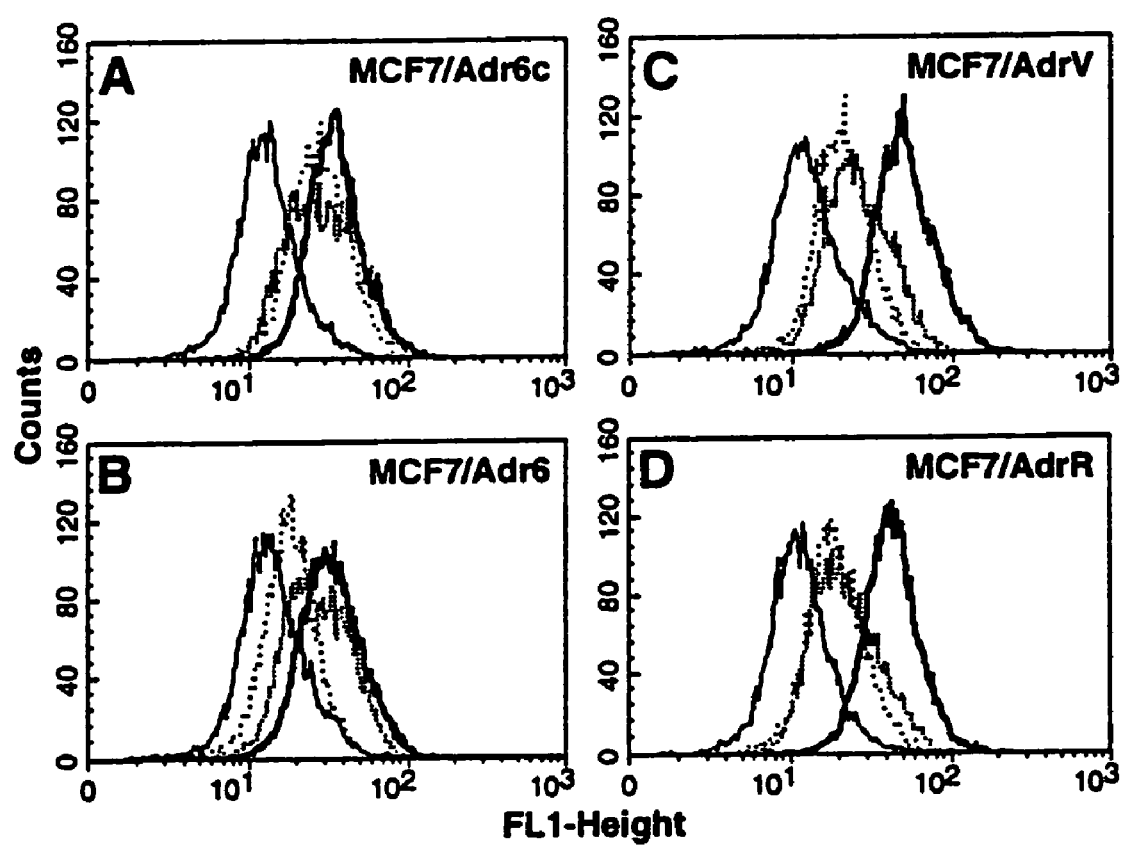

FIG. 8 depicts the results of a flow cytometry experiment measuring retention of doxorubicin in MCF7/AdrR cells transfected with pcDNA/RAB6C (panel A), pcDNA/RAB6 (panel B), or pcDNA1.1/Amp (control, panelC), compared with non-transfected cells (panel D). In each graph, the solid thin line represents untreated cells, the solid bold line represents cells loaded with doxorubicin for 2 hours. The dotted thin and bold lines represent doxorubicin loaded cells after 3 and 5 hours of chase.

Figure 9:
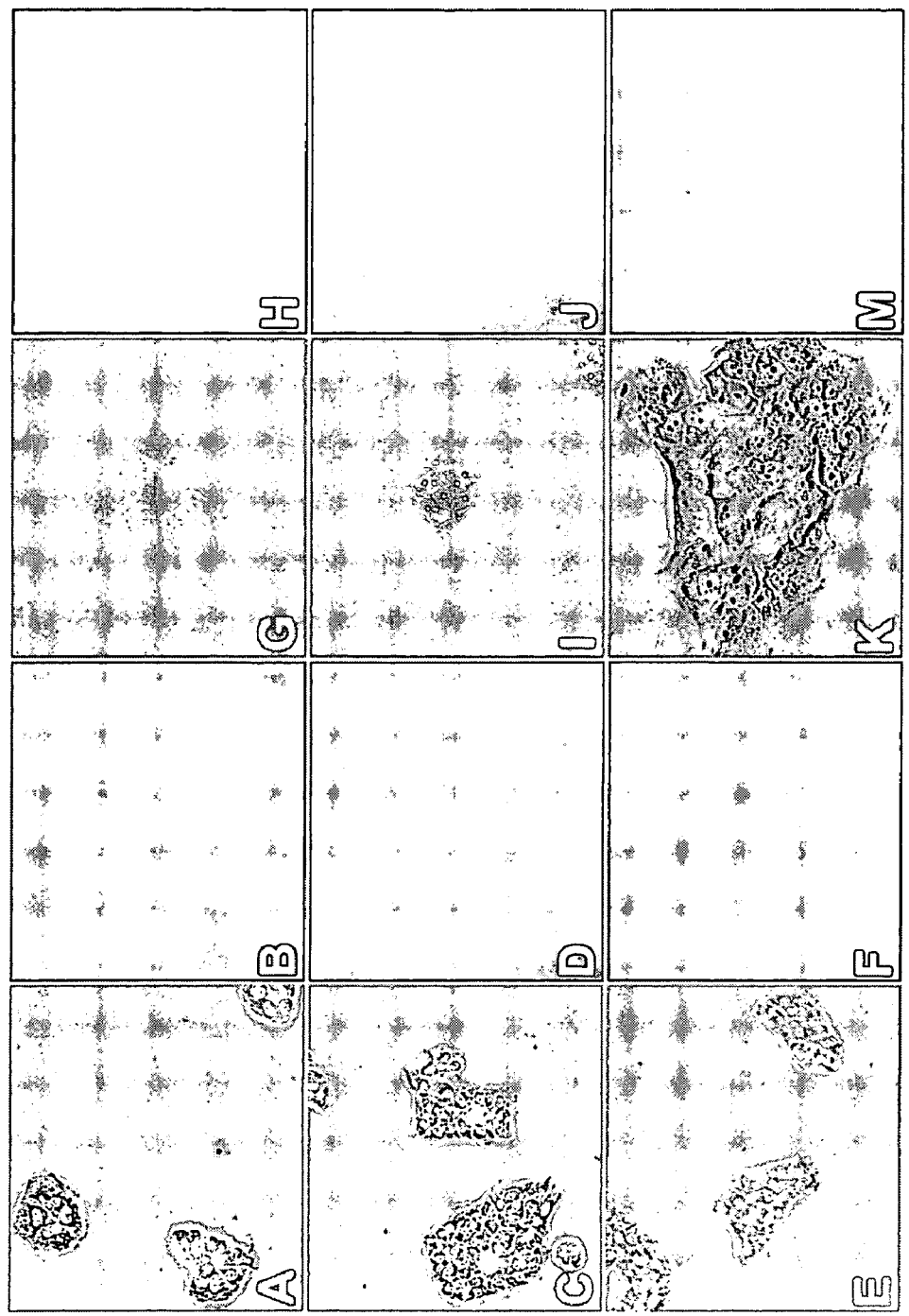

FIG. 9 depicts fluorescence microscopy of MCF7/AdrR cells transfected with pcDNA/RAB6 (A, B, G, H), pcDNA/RAB6C(C, D, I, J) and pcDNA1.1/Amp (E, F, K, M) and loaded for 2 hours with doxorubicin. Panels A, C and E are bright field views at the end of the loading period. Panels B, D, and F show the corresponding fluorescence. Panels G, I, and K are bright field views following a 6 hour chase without doxorubicin. Panels H, J, and M show the corresponding fluorescence. Magnification 150×.

Figure 10:
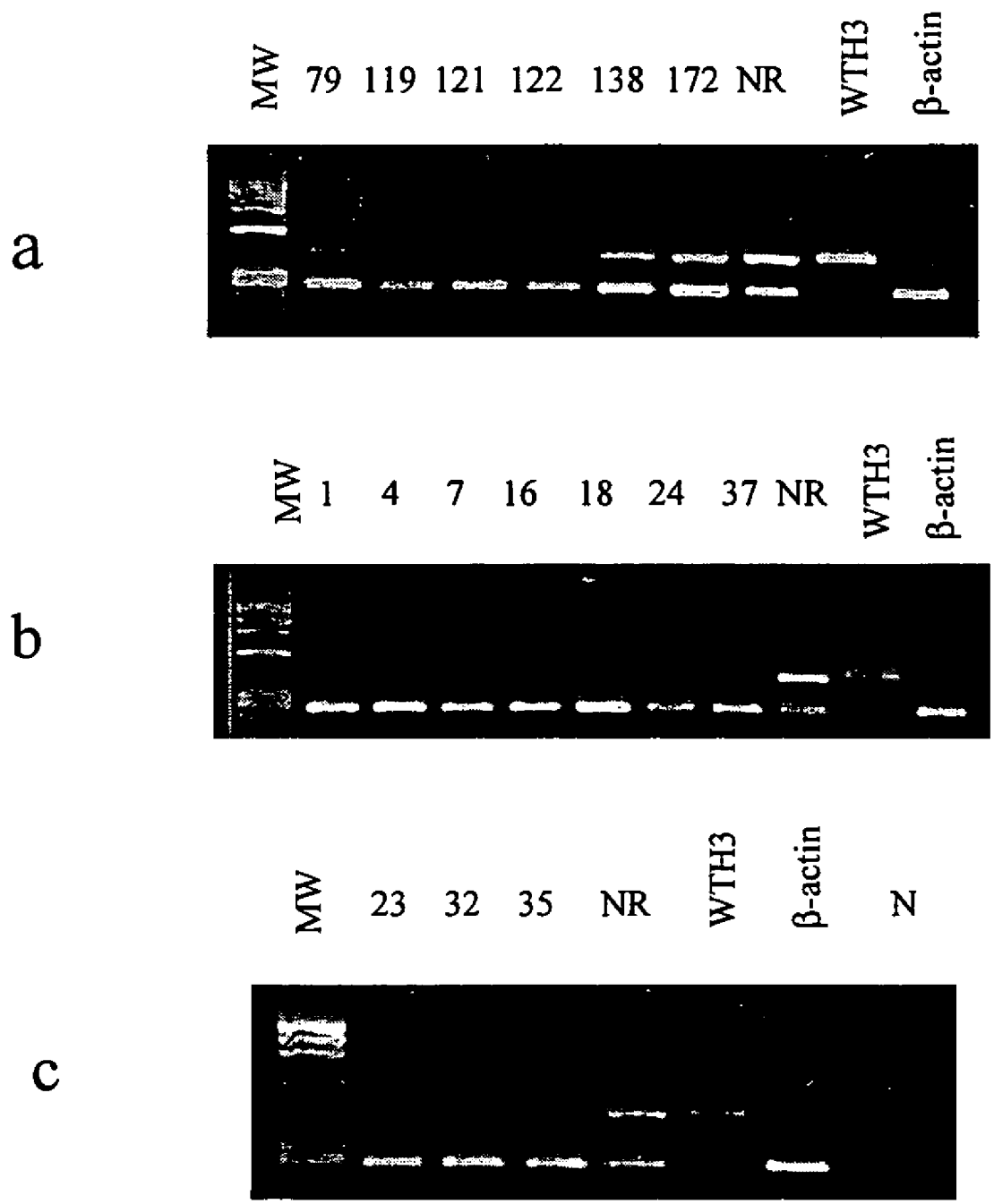

FIG. 10 depicts expression by quantitative PCR of WTH3 mRNA in patients diagnosed with chronic lymphocytic leukemia (CLL; panel a), acute myelogenous leukemia (ALL; panel b), and acute lymphocytic leukemia (ALL; panel c). In each patient sample lane (numbered) the 343 bp product generated with WNT3 specific primers is compared with the 495 bp product generated simultaneously with β-actin specific primers. Lanes marked "MW" have a molecular weight standard. Lanes marked "NR" are from a normal control. Lanes marked "WTH3" show quantitive PCR results using a WTH3 standard. Lanes marked "β-actin" show quantitive PCR results using a β-actin standard. Lane "N" is a negative control.

DETAILED DESCRIPTION OF THE INVENTION

The present invention is directed to genomic loci which are differentially methylated in multiple drug resistant cells compared to non-multiple drug resistant cells. One of the present genomic loci is WTH3, which is homologous to a known locus, the RAB6 locus. The WTH3 genomic locus has a nucleotide sequence which comprises SEQ ID NO:7, and encodes an open reading frame. The complete coding sequence of the wth3 protein is represented by SEQ ID NO:11. The encoded 254 amino acid wth3 protein is represented by SEQ ID NO:12.

The present WTH3 genomic locus was isolated by Methyl-Differential Display ("MDD") methods as disclosed in U.S. Ser. No. 08/657,866, filed May 31, 1996, which is hereby incorporated by reference. MDD is used for detecting and isolating DNA fragments that are normally methylated in one cell type, but which, for some reason, are hypo- or hyper-methylated in another cell type. Such DNA fragments may normally be methylated for a number of reasons. For example, such DNA fragments may be normally methylated because they contain, or are associated with, genes that are rarely expressed, genes that are expressed only during early development, genes that are expressed in only certain cell-types, and the like. According to the present invention, the WTH3 locus is hypermethylated in drug resistant cells relative to non-drug resistant cells. Moreover, multiply drug resistant cells express less WTH3 mRNA than non-drug resistant cells.

Hence, the present nucleic acids can be used to detect aberrant expression in cells suspected of being multiply drug resistant. Moreover, the present nucleic acids can be used for detecting hypomethylation, hypermethylation or a mutation in homologous DNA fragments. Similarly, the present genomic nucleic acids can be used to detect expression of homologous mRNAs and to isolate homologous cDNAs.

As used herein, hypomethylation means that at least one cytosine in a CG or CNG di- or tri-nucleotide site in genomic DNA of a given cell-type does not contain $CH_3$ at the fifth position of the cytosine base. Similarly, as used herein, hypermethylation means that at least one cytosine in a CG or CNG di- or tri-nucleotide site in genomic DNA of a given cell-type does contain $CH_3$ at the fifth position of the cytosine base.

Cell types which may have hypo- or hyper-methylated CGs or CNGs include any cell type which may be expressing a tissue-specific, cell-type specific or non-housekeeping gene. This includes both normal cells that express tissue-specific or cell-type specific genetic functions, as well as tumorous, cancerous, and similar cell types. Cancerous cell types and conditions which can be analyzed or diagnosed by the present methods include Wilm's cancer, breast cancer, ovarian cancer, colon cancer, kidney cell cancer, liver cell cancer, lung cancer, leukemia, rhabdomyosarcoma, sarcoma, and hepatoblastoma. Test cell types can therefore include cells that express tissue or cell-specific functions, cancer cells, tumor cells and the like.

A control cell type may be simultaneously tested. Such a control cell type is preferably an undiseased cell of the same cell type as the test cell. For example, if breast cancer cells are selected as the test cell type, the normal cell type would be breast cells that are not diseased or cancerous. Preferably, test and normal cell types are isolated from the same person. Test sample and control sample nucleic acids can be obtained from any mammalian body fluid, secretion, cell-type, or tissue, as well as any cultured cell or tissue.

According to the present invention, a mutation, hypomethylation and hypermethylation at a specific site in genomic DNA can be detected by observing whether the size or intensity of a DNA fragment cut with a methylation sensitive restriction enzyme is the same in control and test samples. This can be done by cutting genomic DNA isolated from control and test tissue samples with the methylation-sensitive ("master") restriction enzyme, hybridizing a probe to the control and test DNAs and observing whether the two hybridization complexes are the same or different in size or intensity.

After isolation, the test sample and control sample DNA are separately cut with restriction enzymes. For detecting and isolating hypomethylated or hypermethylated DNA sites, a methylation-sensitive restriction enzyme should be used. The selection of a methylation-sensitive restriction enzyme for the practice of the present invention is within the skill of an artisan in the field. Cleavage methods and information for selecting restriction enzymes for cutting DNA at specific sites are known to the skilled artisan. For example, many suppliers of restriction enzymes provide information on conditions and types of DNA sequences cut by specific restriction enzymes, including New England BioLabs, ProMega Biochem, Boehringer-Mannheim and the like. Sambrook et al. provide a general description of methods for using restriction enzymes and other enzymes. See Sambrook et al., 1989 *Molecular Cloning: A Laboratory Manual*, Vol. 1–3 (Cold Spring Harbor Press, Cold Spring Harbor, N.Y.). In one embodiment, the Msp I restriction enzyme is used which recognizes and cleaves DNA at nonmethylated CCGG but will not cleave the CCGG sequence when the outer cytosine is methylated. Other methylation sensitive enzymes contemplated by the present invention include Hpa II BsiS I, Hin2 I and the like.

Nucleic acids homologous to the present WTH3 nucleic acid can be detected by any procedure available to one of skill in the art. For example, hybridization techniques are frequently used for detecting nucleic acids and the present invention contemplates all available hybridization techniques, including Southern, Northern and in situ hybridization techniques.

In particular, the present invention provides a method for detecting whether a CG or CNG sequence is hypomethylated or hypermethylated in a genomic DNA homologous to WTH3 which is present in a test sample of cells. This method includes:
   a) isolating genomic DNA from a control sample of cells and a test sample of cells to generate a control-cell DNA and a test-cell DNA;
   b) cleaving the control-cell DNA and the test-cell DNA with a methylation-sensitive restriction enzyme to generate cleaved control-cell DNA and cleaved test-cell DNA;
   c) preparing a probe capable of hybridizing to a WTH3 nucleic acid or a homologous nucleic acid known to demonstrate cell-type specific methylation patterns;
   d) hybridizing the probe to the cleaved control-cell DNA and the cleaved test-cell DNA is to form a control-hybridization complex and a test-hybridization complex; and
   e) observing whether the size of the control-hybridization complex is the same as the size of the test-hybridization complex.

In one embodiment, the probe may include a WTH3 nucleic acid, which may be selected, for example, from SEQ ID NO:7, SEQ ID NO:10, or SEQ ID NO:11. In another embodiment, the probe can be a RAB6C nucleic acid, for example, SEQ ID NO:24 or SEQ ID NO:25.

Similarly, the present invention provides a method of detecting whether a DNA site is mutated in a genomic DNA homologous to a WTH3 nucleic acid which is present in a test sample of cells. This method includes:
   a) isolating genomic DNA from a control sample of cells and a test sample of cells to generate a control-cell DNA and a test-cell DNA;
   b) cleaving the control-cell DNA and the test-cell DNA with a detector restriction enzyme to generate cleaved control-cell DNA and cleaved test-cell DNA;
   c) preparing a probe from a discrete DNA isolated by the methods of the present invention;
   d) hybridizing the probe to the cleaved control-cell DNA and the cleaved test-cell DNA to form a control-hybridization complex and a test-hybridization complex; and
   e) observing whether the size of the control-hybridization complex is the same as the size of the test-hybridization complex;

wherein the detector restriction enzyme does not cleave a mutated DNA site but does cleave a corresponding nonmutated DNA site.

The skilled artisan can vary the hybridization conditions used for detecting homologous nucleic acids to achieve optimal hybridization. Conditions for achieving optimal hybridization are known to the skilled artisan and generally include probe length, temperature and salt concentrations permitting selective hybridization between two highly homologous DNA fragments, e.g. stringent hybridization conditions. Stringent conditions permit little or no detectable hybridization between mismatched driver or tester fragments, that is between fragments that have dissimilar sequences, particularly at the ends. Hybridization techniques are described, for example, in Sambrook et al., 1989 *Molecular Cloning: A Laboratory Manual*, Vols. 1–3 (Cold Spring Harbor Press, Cold Spring Harbor, N.Y.).

It is well known in the art to adjust hybridization and wash solution salt conditions and temperatures such that stringent hybridization conditions are obtained. Preferred stringent conditions are those that allow a probe to hybridize to sequences which are more than 90% complementary to the probe and not to those which are less than 70% complementary. Stringency depends on such parameters as the size and nucleotide content of the probe being utilized. See Sambrook et al. and other sources for general descriptions and examples.

Hybridization techniques for detecting specific genomic DNA fragments are known in the art and include solid-phase-based hybridization and solution hybridization which use any of the known reporter molecules. Detailed methodology for gel electrophoretic and nucleic acid hybridization techniques can be found in Sambrook et al.

Using the nucleotide sequences provided herein, probes can be constructed which are useful as reagents for detecting the susceptibility of particular DNA sequences in a test sample to cleavage by restriction endonucleases. Such susceptibility to cleavage is affected by factors which include methylation of particular bases and the substitution of bases through mutation. For example, from the sequences provided, it is possible to generate nucleic acid probes to determine the sizes and relative amounts of particular DNA species which result when DNA recovered from a test sample is digested with selected sequence specific endonucleases. Preferred nucleic acid probes for detecting hypomethylation, hypermethylation and mutation of nucleic acids homologous to WTH3 have SEQ ID NOS:7, 10, 11, 24 and 25.

Alternatively, nucleic acid sequences disclosed herein may be used together with the nucleotide sequence of RAB6 to provide nucleic acids which hybridize preferentially to RNA or DNA molecules which have greater or lesser homology to RAB6 than to WTH3. For example, nucleic acid probes which are homologous to RAB6 and not to WTH3 are useful for detection of nucleic acids which are homologous to RAB6 and not WTH3. RAB6c, as disclosed herein, is an example of a gene which displays an overall homology to RAB6, but which possesses one region which is more homologous to WTH3 than to RAB6. It is easy for one of skill in the art to make use of sequences disclosed herein to select or design probes and primers which are capable of hybridizing with WTH3 nucleotides and not RAB6 nucleotides, or capable of hybridizing with RAB6 nucleotides and not WTH3 nucleotides, or capable of hybridizing with both WTH3 nucleotides and RAB6 nucleotides.

According to the present invention, a nucleic acid of the present invention can be labeled by any procedure known in the art to create a probe, for example, by incorporation of nucleotides linked to a "reporter molecule".

A "reporter molecule", as used herein, is a molecule which provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes can be conjugated to avidin or streptavidin for use with a biotinylated probe. Similarly, probes can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or tolidine are commonly used.

Incorporation of a reporter molecule into a DNA probe can be by any method known to the skilled artisan, for example by nick translation, primer extension, random oligo priming, by 3' or 5' end labeling or by other means (see, for example, Sambrook et al.).

In another embodiment, the present invention provides one or more compartmentalized kits for detection of hypomethylation, hypermethylation or mutation of nucleic acids homologous to the present WTH3 nucleic acids. The kit has a receptacle containing at least one of the present probes. Such a probe is capable of hybridizing to DNA sequences at or adjacent to mutated or abnormally methylated WTH3 DNA. Alternatively, a probe can be provided which binds preferentially to DNA sequences at or adjacent to mutated or abnormally methylated RAB6 DNA. The probe provided in the present kits may have a covalently attached reporter molecule.

The present invention further contemplates detecting and isolating nucleic acid homologous to the present WTH3 nucleic acid by nucleic acid amplification. Nucleic acid amplification procedures for use in the present invention include any in vitro amplification procedure which provides sequence-specific synthesis of a nucleic acid fragment relative to the complex bulk of nucleic acid present in a sample. The specificity of the process is determined by enzymatic recognition of a specific sequence or by the oligonucleotide primers which are capable of hybridizing only with the present nucleic acids.

In vitro DNA amplification techniques are known in the art. A review of such techniques can be found in Kwoh et al., 8 Am. Biotechnol. Lab. 14 (1990). In vitro nucleic acid amplification techniques include polymerase chain reaction (PCR), transcription-based amplification system (TAS), self-sustained sequence replication system (3SR), ligation amplification reaction (LAR), ligase-based amplification system (LAS), Qβ RNA replication system and run-off transcription.

PCR is a preferred method for DNA amplification. PCR synthesis of DNA fragments occurs by repeated cycles of heat denaturation of DNA fragments, primer annealing onto the adaptor ends of the master-cut DNA fragment, and primer extension. These cycles can be performed manually or, preferably, automatically. Thermal cyclers such as the Perkin-Elmer or Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment.

PCR techniques and many variations of PCR are known. Basic PCR techniques are described by Saiki et al. (1988 Science 239:487–491) and by U.S. Pat. Nos. 4,683,195, 4,683,202 and 4,800,159, which are incorporated herein by reference.

The size range of DNA fragments in a sample of genomic DNA is that size range which can be amplified by in vitro DNA amplification. When polymerase chain reaction ("PCR") is used, that size range is about 2000 base pairs (bp) to about 75 bp. Preferably the selected size range is about 1500 bp to about 100 bp. More preferably the selected size is about 1000 bp to about 150 bp.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, Thermus aguaticus or Thermococcus litoralis DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, Escherichia coli DNA polymerase I, Klenow fragment of E. coli DNA polymerase I, T4 DNA polymerase, T7 DNA polymerase, Thermus aquaticus (Taq) DNA polymerase, Thermococcus litoralis DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, E. coli DNA ligase or Qβ replicase. Preferred amplification enzymes are the pwo and Taq polymerases. The pwo enzyme is especially preferred because of its fidelity in replicating DNA.

The length of the primers for use in PCR depends on several factors including the nucleotide sequence and the temperature at which these nucleic acids are hybridized or used during in vitro nucleic acid amplification. The considerations necessary to determine a preferred length for an oligonucleotide primer are well known to the skilled artisan. For example, as is known to the skilled artisan, the length of a short nucleic acid or oligonucleotide can relate to its hybridization specificity or selectivity. Because the tester and driver samples contain a complex mixtures of nucleic acids, primers which are shorter than about 12 nucleotides may hybridize to more than one site in the test genomic DNA, and accordingly would not have sufficient hybridization selectivity for amplifying only the master-cut fragments. However, a 12- to 15-nucleotide sequence is generally represented only once in a mammalian genome (Sambrook et al. 1989 Molecular Cloning: A Laboratory Manual, Vol. 2, Cold Spring Harbor Press, Cold Spring Harbor, N.Y.; pp. 11.7–11.8). Accordingly, to eliminate amplification of fragments which do not have adaptors, primers are chosen which are generally at least about 14 nucleotides long. Preferably, the present primers are at least 16 nucleotides in length. More preferred primers are at least 17 nucleotides in length (Sambrook et al., pp. 11.7–11.8).

The genomic nucleic acids isolated by the present invention, or oligonucleotides obtained therefrom, can also be used for detecting or measuring expression products, for example, mRNAs, complementary DNAs (cDNAs) and proteins derived from the present genomic nucleic acids and cDNAs. Expression products which may be detected or measured also include those having incomplete homology to the disclosed nucleotide and amino acid sequences.

Expression of mRNAs homologous to the nucleic acids of the present invention may be detected, for example, by Northern analysis, or by reverse transcription and amplification by PCR. Also contemplated are nucleic acid detection and quantification methods which employ signal moieties that are conjugated to nucleic acid probes. Nucleic acids in a sample can be immobilized on a solid support and hybridized to such probes. The signal moiety can be detected directly, for example by fluorescence. Alteratively, the signal moiety may be detected indirectly by its enzymatic activity, for example in an ELISA or other colorimetric assay.

Useful procedures permit detection of mRNAs in a variety of tissue types or at different stages of development. The subject nucleic acids which are expressed in a tissue-specific or a developmental-stage-specific manner are useful as tissue-specific markers or for defining the developmental stage of a sample of cells or tissues. One of skill in the art can readily adapt the present nucleic acids and oligonucleotides for these purposes.

Useful hybridization conditions for probes and primers made according to the present invention are readily determinable by those of skill in the art. Generally, preferred stringent hybridization conditions are those which allow hybridization of nucleic acids which are greater than 90% homologous but which prevent hybridization of nucleic acids which are less than 70% homologous. In situations where nucleic acids belong to families in which extensive homologies exist, it may be desired to further increase stringency of hybridization conditions. Guidelines for predicting melting temperatures of nucleic acid duplexes, whether 100% complementary or containing various numbers of mismatches, are well known in the art. See, e.g. Sambrook et al., 1982 *Molecular Cloning: A Laboratory Manual*, 388 (Cold Spring Harbor Press, Cold Spring Harbor, N.Y.) and included references.

In another embodiment of the present invention, cDNAs homologous to the present nucleic acids can be isolated by procedures readily available to those of skill in the art. For example, cDNA libraries can be obtained from the tissues or cells which express the present genomic nucleic acids. Those cDNA libraries can then be probed with a genomic nucleic acid isolated by the methods of the present invention, or an oligonucleotide fragment thereof. Again, one of skill in the art can readily isolate such cDNAs using the genomic nucleic acids of the present invention.

The present genomic and cDNA nucleic acids can be used to prepare oligonucleotides. In one embodiment, oligonucleotides having twelve nucleotides or more can be prepared which hybridize specifically to the present genomic nucleic acids and cDNAs and allow detection and isolation of unique nucleic sequences by hybridization. Sequences of at least 15–20 nucleotides are preferred and are selected from regions which lack homology to other known sequences. Sequences of 20 or more nucleotides which lack such homology are optimal.

Genomic nucleic acids provided by the present invention which include portions of WTH3 (e.g., SEQ ID NOS:7, 10, 11, 13, 14, 15, 16, 17, 18) correspond to a genomic region which is hypermethylated in a drug resistant cell line. Each of these nucleic acids is useful for detecting hypomethylation, hypermethylation and expression of homologous nucleic acids in a variety of normal and cancerous cells or tissues. Each of these nucleic acids is also useful for identifying homologous genomic and cDNA nucleic acids.

Oligonucleotides useful as probes for screening of samples by hybridization assays or as primers for amplification can be packaged into kits. Such kits usually contain the probes or primers in a premeasured or predetermined amount, as well as other suitably packaged reagents and materials needed for the particular hybridization or amplification protocol. In an embodiment of the invention, nucleic acids of the invention are used to detect expression of WTH3, RAB6C, RAB6 or homologous genes by quantitative PCR. When expression of WTH3 is to be determined, preferred primers are 5'-GATGGAACAATCGGGCTTCG-3' (SEQ ID NO:40) and 5'-GTAGCAGGAACAACCCCCT-TCG-3' (SEQ ID NO:42). When expression of RAB6C is to be determined, preferred primers are 5'-GATCGAACAAT-CAGGCTTCAG-3' (SEQ ID NO:43) and 5'-AAGGGGGC-CAAAGCAGTGAGC-3' (SEQ ID NO:44). When expression of RAB6 is to be determined, preferred primers are 5'-GGATCGAACAGTACGATTGC-3' (SEQ ID NO:45) and 5'-GCTGCTGCTACACGTCGAAAGAG-3' (SEQ ID NO:46).

In an embodiment of the invention, samples from patients are tested to determine expression or WTH3, RAB6C, RAB6 or a homolog. As used in this context, a homolog is a nucleic acid sequence which encodes a protein having about 80% or greater amino acid sequence identity to wth3, or rab6c, or rab6 over the length of the protein which corresponds to rab6. More preferably, a homolog has about 90% or greater sequence identity over the length of the protein which corresponds to rab6. In a preferred embodiment, expression of one or more of these genes is compared to expression of a constitutively expressed gene. Expression of the constitutively expressed gene encoding β-actin is commonly measured for this purpose. Expression of other constitutively express genes can be measured instead for this purpose.

In a preferred embodiment, expression of WTH3, or RAB6C, or RAB6, or a homolog in cancer cells is tested. Examples of cancer cells are chronic lymphocytic leukemia (CLL) cells, acute myelogenous leukemia (AML) cells and acute lymphocytic leukemia (ALL) cells. Expression of any one of these genes is useful as an indication of whether the cancer will be susceptible to treatment with certain drugs. For example, where expression of any one of these genes is reduced two fold with respect to expression in a normal control, resistance to doxorubicin and various other therapeutics which are substantially ineffective for treatment of MDR cancers will be expected and other therapeutics will be used instead. Therapeutics which are substantially ineffective for treatment of MDR cancers include, but are not limited to vinblastin, vincristine, taxol, cis-platin, etoposide, dactinomycin, gramicidin D and 5-fluorouracil. The critical deficiency of expression which differentiates a MDR cell may be larger than two fold. However, it is to be remembered that in a sample of cells from a patient, for example cells from a tumor, or peripheral blood cells, only a small proportion of cells may have acquired drug resistance. A two-fold deficiency in expression from such a sample can indicate that a significant portion of the cancer cells has become resistant to doxorubicin and other drugs.

In another embodiment, the present genomic and cDNA nucleic acids can be placed in expression vectors capable of expressing an encoded protein, polypeptide or peptide. Nucleic acids encoding a desired protein or polypeptide are derived from cDNA or genomic clones using conventional restriction digestion or by synthetic methods, and are ligated into vectors from which they may be expressed. Vectors may, if desired, contain nucleic acids encoding portions of other proteins, thereby providing a fusion protein. For example, portions of the β-galactosidase or superoxide dismutase coding region may be placed in frame with the present coding regions to provide an expression vector which encodes a fusion protein.

Expression vectors include plasmids designed for the expression of proteins or polypeptides fused to or within bacterial phage coat proteins. The DNA encoding the desired protein or polypeptide, whether in a fusion, premature or mature form, may be ligated into expression vectors suitable for any host. The DNA encoding the desired polypeptide may also contain a signal sequence to permit secretion from the intended host. Both prokaryotic and eukaryotic host systems are contemplated.

The present proteins, polypeptides and peptides, whether in a premature, mature or fused form, are isolated from lysed cells, or from the culture medium, and are purified to the extent needed for the intended use. One of skill in the art can readily purify these proteins, polypeptides and peptides by any available procedure. For example, purification may be accomplished by salt fractionation, size exclusion chromatography, ion exchange chromatography, reverse phase chromatography, affinity chromatography and the like.

The present invention further contemplates antibodies which can bind to the present proteins, polypeptides and peptides. Such antibodies preferably bind to unique antigenic regions or epitopes in the present proteins, polypeptides and peptides.

Epitopes and antigenic regions useful for generating antibodies can be found within the present proteins, polypeptides or peptides by procedures available to one of skill in the art. For example, short, unique peptide sequences can be identified in the present proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the present proteins and polypeptides. These surface epitopes are more readily detected in samples tested for the presence of the present proteins and polypeptides.

Peptides can be made by any procedure known to one of skill in the art, for example, by using in vitro translation or chemical synthesis procedures.

Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art can use available procedures and coupling reagents to link the desired peptide epitope to such a carrier. For example, coupling reagents can be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies can vary widely. The minimum size must be sufficient to provide an antigenic epitope which is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 10, 12 or 15 amino acids, up to a maximum of about 20 or 25 amino acids.

Amino acid sequences comprising useful epitopes can be identified in a number of ways. For example, the entire protein sequence can be screened by preparing a series of peptides that together span the entire protein sequence. One of skill in the art can routinely test a few large polypeptides for the presence of an epitope showing a desired reactivity and also test progressively smaller and overlapping fragments to identify a preferred epitope with the desired specificity and reactivity.

In some situations where a high degree of homology exists among various proteins of a family, useful epitopes will be defined as those which identify one particular member of the protein family, and will correspond to regions of the protein of interest where there is no known homology to other proteins. In those cases, it may be desirable to express only the unique predefined epitopes, for example as part of a fusion protein or displayed on the surface of a filamentous phage particle which can then be used to produce antibodies. Alternatively, monoclonal antibodies can be screened to identify those that bind to the unique epitope and not to epitopes common within the protein family. Similarly, polyclonal antibody preparations may be reacted with other members of the protein family to subtract antibodies which bind to common epitopes.

Antigenic polypeptides and peptides are useful for the production of monoclonal and polyclonal antibodies. To obtain polyclonal antibodies, a selected animal is immunized with a protein or polypeptide. Serum from the animal is collected and treated according to known procedures. Polyclonal antibodies to the protein or polypeptide of interest may then be purified by affinity chromatography. Techniques for producing polyclonal antisera are will known in the art.

Monoclonal antibodies may be made by procedures available to one of skill in the art, for example, by fusing antibody producing cells with immortalized cells and thereby making a hybridoma. The general methodology for fusion of antibody producing B cells to an immortal cell line is well within the province of one skilled in the art.

The present antibodies are useful for detecting the present proteins and polypeptides in specific tissues or in body fluids. Moreover, according to the present invention, detection of aberrantly expressed proteins or protein fragments is probative of a disease state. For example, expression of the present proteins or polypeptides from a hypomethylated genomic locus may indicate that the protein is being expressed in an inappropriate tissue or at an inappropriate developmental stage. Hence, the present antibodies are useful for detecting diseases associated with protein expression from improperly methylated genomic loci, for example, the types of cancers and genetic diseases contemplated herein.

Design of immunoassays is subject to a great deal of variation and a variety of these are known in the art. Immunoassays may use a monoclonal or polyclonal antibody reagent which is directed against one epitope of the antigen being assayed. Alternatively, a combination of monoclonal or polyclonal antibodies may be used which are directed against more than one epitope. Protocols may be based, for example, upon competition, direct antigen-antibody reaction or sandwich type assays. Protocols may, for example, use solid supports or immunoprecipitation. The present antibodies can be labeled with a reporter molecule for easy detection. Assays which amplify the signal from a bound reagent are also known. Examples include immunoassays which utilize avidin and biotin, or which utilize enzyme-labeled antibody or antigen conjugates, such as ELISA assays.

Kits suitable for immunodiagnosis and containing the appropriate labeled reagents include antibodies directed against the present protein epitopes or antigenic regions, packaged appropriately with the remaining reagents and materials required for the conduct of the assay, as well as a suitable set of assay instructions.

Nucleic acids which are homologous to WTH3, RAB6C, or RAB6 can be useful for treatment of cells and tumors exhibiting multiple drug resistance. For example, drug resistant cells transfected with a vector which expresses WTH3, RAB6C, or RAB6 demonstrate an increased sensitivity to doxorubicin as compared to cells transfected with a control vector. In MCF7/AdrR cells where multiple transcripts homologous to WTH3, RAB6C, or RAB6 are present in less than normal amounts, multidrug resistance, including resistance to doxorubicin, may not be a direct result of underexpression of WTH3, or of RAB6C, or of RAB6, or of homologs. Nevertheless, increasing expression of any one the genes results in increased sensitivity to doxorubicin. Inhibition of doxorubicin resistance which is observed in cells which overexpress WTH3, RAB6C, or RAB6 is likely to be observed for cells which overexpress homologous genes, as well.

In another embodiment of the invention, a cell which overexpresses wth3, rab6c, rab6 or a homologous protein is used in a screening method which identifies modulators of drug resistance or modulators of multidrug resistance. The cells can also be used to identify modulators of other phenotypes as well. Other useful phenotypes are those which can result from, or be affected by the overexpression of wth3, rab6c, rab6 or a homolog. Useful cells which overexpress the proteins usually contain an expression vector which comprises an exogenous expressible gene which encodes wth3, rab6c, rab6 or a homolog. Alternatively, a cell can be used which has been shown to have increased levels of one or more of the aforementioned proteins. Substances which are modulators of multidrug resistance can exert their effect by increasing expression of wth3, rab6c, rab6 or a homolog from either or both of the endogenous chromosomal gene and the exogenous gene. Alternatively, the modulating substance can affect the protein directly.

To perform such a screening method, the test cell is incubated with an amount of a therapeutic substance to which it would otherwise be tolerant and an amount of the candidate modulator. For example, a cell expressing wth3, rab6c, rab6 or a homolog can be incubated with an amount of doxorubicin which allows continued cell growth and an amount of the test substance. When the therapeutic is doxorubicin, the amount to be used will depend on the test cell. For example, $IC_{50}$ for doxorubicin for MCF7/AdrR cells carrying endogenously expressed RAB6C can be about 1.0 µM to about 2.5 µM. The concentration of doxorubicin to use would be low enough to allow observable cell growth. It is well known to one of ordinary skill in the art to choose an effective concentration of doxorubicin. Modulators which increase sensitivity of the cells to doxorubicin can be identified by looking for substances which result in cell morbidity. Cells are observed over a period of time and under conditions in which growth of the test cell in the absence of candidate modulator is apparent.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

Examples of the invention which follow are set forth to further illustrate the invention and should not be construed to limit the invention in any way.

EXAMPLE 1

Altered Methylation Patterns at CpG Dinucleotides in Cells Exhibiting Multiple Drug Resistance Methylation sensitive MDD was employed to detect differences in methylation between DNAs isolated from drug resistant MCF7/AdrR cells (resistant to doxorubin) and the parental human breast cancer cell line MCF7.

Isolation of a Hypermethylated DNA Fragment from MCF7 Human Breast Cancer Cell Line. DNAs isolated from MCF7/AdrR and MCF7 cell lines (available from National Institutes of Health, Bethesda, Md.) were cleaved by the Hpa II enzyme. To study DNA hypermethylation events, cleaved MCF7 DNA was used as tester, while cleaved MCF7/AdrR was used as driver. 1 µg of DNA tester and driver were cleaved with Hpa II (20 U/µg) (Boehringer Mannheim) in a 200 µl reaction for 3 hours. To prepare tester and driver amplicons, the digested tester and driver DNAs were ligated to MSA24-mer (SEQ ID NO:1) and MSA12-mer (SEQ ID NO:2). The procedures for amplicon preparation were as described in N. A. Lisitsyn et al., *Direct Isolation of Polymorphic Markers Linked to a Trait by Genetically Directed Representational Difference Analysis,* 6 NATURE GENETICS 57 (1994). The DNA amplicons were then purified by phenol, phenol/chloroform extraction. To remove the first set of linkers from the driver amplicon, 80 µg of driver amplicon DNA was digested with the Hpa II enzyme (10 U/µg). To change the tester amplicon DNA linkers, 5 µg of tester amplicon was digested with Hpa II (10 U/µg), and ligated to MSB24-mer (SEQ ID NO:3), and MSB12-mer (SEQ ID NO:4), a second set of oligonucleotide linkers. Subtractive hybridization was performed, followed by Polymerase Chain Reaction (PCR) amplification of the first round difference products (DP1) which was carried out as described in Lisitsyn, N. et al. (1994). To prepare the second round of subtractive hybridization, 3 µg of DP1 was digested with the restriction endonuclease Hpa 11 (10 U/µg), and ligated to third set of linkers, MSC24-mer (SEQ ID NO:5) and MSC12-mer (SEQ ID NO:6). Another round of subtractive hybridization/PCR amplification was performed. The second difference product (DP2) was amplified as before. The individual DNA fragments in DP2 were purified by DNA gel extraction kit (Qiagen Inc.), ligated into plasmid vector pUC118 linearized by the restriction endonuclease Acc I, and transformed into *E. coli* (DH5α). Plasmid DNAs were isolated from twelve colonies, and served as templates to amplify the inserts by PCR. Different sized inserts were selected as probes for amplicon Southern analysis. The candidate probes were further tested by genomic DNA Southern analysis.

Amplicon DNA Southern analysis. A candidate probe was identified which hybridized to tester amplicon DNA but not to driver amplicon DNA. The first screen for identification of candidate probes was performed with amplicon DNA Southern blots. A non-Radiation DIG Labeling and Detection Kit was purchased from Boehringer Mannheim. Probe labeling, and detection followed the instructions of the manufacturer. 2 µg of tester and driver amplicon DNA were electrophoresed on a 2% agarose gel, and blotted to positively charged nylon membranes (Boehringer Mannheim). For prehybridization the membranes were placed at 68° C. for 2–4 hours in solutions containing 5× SSC, 0.1% of N-lauroylsarcosine, 0.02% of SDS, 1% of blocking reagent. Under the same conditions, the probes were added, and hybridized to the membranes overnight. The membranes were then rinsed with 2× SSC, 0.1% SDS for 5 min twice at room temperature, then washed twice with 0.1× SSC, 0.1% SDS for 15 min at 68° C. Next, the membranes were equilibrated in maleic acid buffer (0.1 M maleic acid, 0.15 M NaCl, pH 7.5) then transferred into blocking solution (1% black reagent in maleic acid buffer) and incubated at room temperature for 30 min. The membranes were then incubated for 30 min in antibody solution (75 mU/ml of anti-DIG-AP conjugate in blocking solution). After the membranes were equilibrated 2–5 min in detection buffer (0.1 M Tris-HCl, 0.1 M NaCl, 50 mM $MgCl_2$, pH 9.5), the color was developed in freshly prepared color solution (45 µl NBT solution, 35 µl X-phosphate solution in 10 ml of detection buffer). When the desired color intensities were achieved, the reaction was stopped by washing the membranes with 50 ml of water for 5 min. A probe designated WTH3 was identified which hybridized only to tester amplicon DNA.

Genomic DNA Southern analysis. The candidate probes confirmed by amplicon DNA Southern blot experiments was further tested by MCF7/AdrR and MCF7 genomic DNA Southern blotting. 6 µg of genomic DNA was digested with Hpa II (20 U/µg) for 4 hours, and electrophoresed on a 1% agarose gel. Digested DNA was then transferred to a Hybond N-membranes (Amersham, Arlington Heights, Ill.) which were then exposed to UV light to immobilize the DNA. The probe for the Southern blot was labeled using a High Prime DNA labeling kit (Boehringer Mannheim) following the instructions of the manufacturer. For prehybridization, the membranes were placed at 68° C. for 2–4 hours in solutions containing 6× SSC, 5× Denhardt's solution, 0.5% SDS, 0.1 M EDTA, and 50 µg/ml of salmon sperm DNA. Under the same conditions, probe was added, and hybridized to the membranes overnight. The membranes were then rinsed three times with 2× SSC, 1× Blot wash (12 mM $Na_2HPO_4$, 8 mM $NaH_2PO_4$, 1.4 mM $Na_4P_2O_7$, 0.5% SDS) at 68° C., and further washed three times (30 minutes each) with the same buffer at 68° C. The membranes were exposed on Kodak X-OMAT films overnight.

The Southern blot results showed that probe WTH3 hybridized an approximately 600 bp length single band in the MCF7 DNA but not in the MCF7/AdrR DNA. However, at this point, we could not conclude that the differences observed were caused by differential DNA methylation in the two cell lines, since similar hybridization patterns could be the results of either DNA point mutations or deletions. To identify the cause, Southern analysis was performed on both genomic DNAs which were digested by the Msp I enzyme. Msp I is an isoschizomer of Hpa II, although it is not sensitive to CmCGG. Therefore, Msp I could cleave a methylated site which could not be cut by Hpa II. The results showed that probe WTH3 detected the same hybridization patterns: a single, 600 bp length band appeared in both DNAs. This result suggested that the difference detected by probe WTH3 in the Hpa II digested DNAs represented a hypermethylation event rather than a nucleotide mutation or DNA deletion.

WTH3 is a homolog of the known human gene RAB6 and is located in the q31 region of chromosome 2. The pUC118 plasmid containing the WTH3 probe was sequenced using the Ampli-Cycle sequencing kit (Perkin-Elmer), under conditions described by the manufacturer. Chromosome assignment was determined with Genebridge 4 Radiation Hybrid Panel (Research Genetics, Inc.) by PCR.

DNA sequence analysis showed that probe WTH3 contains 573 nucleotides with both ends terminating in Hpa II recognition sites (SEQ ID NO:7). The sequence indicates a gene sequence encoding 175 amino acids and a 47 bp untranslated region at the 5' end. A homology search of the NIH GenBank indicated that the encoded polypeptide shares 89% identity with the first 175 amino acids of the human rab6 protein (GenBank Accession No. M28212), a guanosine triphosphatase (GTPase) containing 208 amino acids. We assume that a 3' end of WTH3 was cut off by digestion with Hpa II. The overall nucleotide sequence homology between the WTH3 genomic clone and RAB6 is high, with sequence differences concentrated within a central region which corresponds to about amino acid 62 through about amino acid 91 of the encoded protein, as shown in FIG. 1.

The 3' end of WTH3 was obtained by a rapid amplification of cDNA ends (RACE) protocol, modified according to Chen, Z., *Simple modifications to increase specificity of the 5' RACE procedure,* 12 TRENDS GENET 87 (1996). Two WTH3 specific primers, W3/Race1 (5'-GATGGAA-CAATCGGGCTTCG-3'; SEQ ID NO:40) and W3/Race2 (5'-AAACAGTCAGCGAAGGGGGT-3'; SEQ ID NO:41) were used in sequential RACE reactions. The nucleotide sequence obtained for the WTH3 locus is represented by SEQ ID NO:10. The coding sequence is represented by SEQ ID NO:11. The gene encodes a protein of 254 amino acids which is represented by SEQ ID NO:12. The homology between the encoded protein and human rab6 is shown in FIG. 2.

The chromosome assignment of WTH3 was determined by amplification from a human genomic DNA library (GENEBRIDGE 4 RH Panel, Research Genetics, Inc.) and the human genome radiation hybrid map of the Whitehead Institute/MIT Center for Genome Research using primers designed to avoid regions of homology between WTH3 and RAB6. One PCR primer (bottom) was designed based on the nonhomologous region located in the middle of the WTH3 gene sequence. The top and bottom strand primer sequences are: 5'-TCCTCTAGTTCCACCATGTCCAC-3' (SEQ ID NO:8) and 5'-CACAGCCGAAGCCCGATTG-3' (SEQ ID NO:9). The map position for WTH3 is 2q31 on the long arm of chromosome 2. The adjacent Sequence Tagged Site (STS) is CHLC.GATA27A12.

Isolation of cDNA and full length coding sequences of WTH3 and RAB6C. The 573 nucleotide WTH3 probe was used to screen cDNA libraries produced from human kidney cells (courtesy of Dr. M. Wigler) and white cell leukemia cells (CLONTECH). Sequence analysis of a number of overlapping clones yielded a composite cDNA sequence of 1460 bp (SEQ ID NO:25). This cDNA has been designated RAB6C. FIG. 3 shows the homology between RAB6C and RAB6. The encoded protein consists of 208 amino acids and differs from the rab6 protein at 3 positions (FIG. 4). Notably, the nucleotide sequence differences between RAB6C and RAB6 are concentrated within the same central region as are the nucleotide sequence differences between WTH3 and RAB6 as disclosed in FIG. 1, which corresponds to about amino acid 62 through about amino acid 91 of the encoded protein.

EXAMPLE 2

Expression of WTH3 and Homologs

Northern analysis. Total RNA was isolated from MCF7/ AdrR and MCF7 cell lines by RNA isolation kit, RNA STAT-60, manufactured by TEL-TEST, Inc. 20 μg of RNA from each cell line was electrophoresed on 1% RNA agarose gels, and then transferred to Hybond N-membranes (Amersham, Arlington Heights, Ill.). The membrane was baked in a vacuum oven at 80° C. for 2 hours to immobilize the RNA. The probes for the northern blot were also labeled with High Prime DNA labeling kits. The procedure for hybridization and blot wash were the same as in the genomic DNA Southern analysis.

Expression of WTH3 is reduced in the MCF7/AdrR cells relative to MCF7 cells. Levels of gene expression of WTH3 in MCF7 and MCF7/AdrR cells were examined by northern analysis. A probe was prepared from the previously described WTH3 containing pUC118 plasmid using primers M13 (5'-GTAAAACGACGGCCAGT-3'; SEQ ID NO:29) and AS (5'-AGCGGATAACAATTTCACACAGGA-3'; SEQ ID NO:30). A probe consisting of a cDNA fragment of the ubiquitously expressed β-actin gene was used as an endogenous control.

The results showed that WTH3 hybridized a 3 kb length band in RNA isolated from both MCF7/AdrR and MCF7 cells. However, the expression level in the MCF7/AdrR cells was about ten times less than that in the MCF7 cells when they were compared to the expressed house keeping gene, β-actin, which hybridized a 2 kb length band in both RNAs (FIG. 5). These results demonstrated that DNA hypermethylation coincided with inhibition of WTH3 gene expression in the MCF7/AdrR cells.

Expression of WTH3 is reduced in peripheral blood cells of leukemia patients. mRNA was prepared from peripheral blood samples from patients having chronic lymphocytic leukemia (CLL), acute myelogenous leukemia (AML), and acute lymphocytic leukemia (ALL). Expression of WTH3 mRNA was determined by quantitative PCR and compared to expression of a constitutively express control mRNA (β-actin). In 6 CLL patients, WTH3 expression was reduced 4 to 100 times as compared to a normal control. In 7 AML patients, expression of WTH3 was reduced 20 to 100 times. In 3 ALL patients, expression of WTH3 was reduced 25 to 100 times. Overall, the amount of decrease in expression was correlated with the severity of the disease and the survival rate of the patients.

Expression of RAB6 related genes is reduced in MDR cells. Expression of RAB6C was determined by two methods. First, northern analysis was used to compare RNA isolated from MCF7/AdrR cells with RNA isolated from MCF7 cells. A 208 bp RAB6 probe consisting of bases 56 to 263 of RAB6 (GenBank Accession No. M28212) was amplified from a cloned fragment using sense and antisense primers 5'-TCCTCTAGTTCCACAATGTCC-3' (SEQ ID NO:31) and 5'-GCAATCGTACTGTTCGATC-3' (SEQ ID NO:32). In order for a quantitative comparison to be made between MCF7/AdrR cells and MCF7 drug sensitive cells, a second probe was prepared which hybridized to glyceraldehyde-3-phosphate dehydrogenase (GPDH). The GPDH probe was amplified using primers 5'-CGGAGTCAACG-GATTTGGTCGTAT-3' (SEQ ID NO:33) and 5'-AGCCT-TCTCCATGGTGGTGAAGAC-3' (SEQ ID NO:34). Surprisingly, a series of different sized RNA species was detected in both RNA preparations (FIG. 6). Equally surprising was the fact that the amount of each transcript detected was reduced in preparations from MCF7/AdrR cells relative to MCF7 cells. The intensities of the resulting bands on the exposed northern blot were quantitatively measured by densitometry and normalized according to the band corresponding to GPDH mRNA. The amount of RAB6 mRNA present in MCF/AdrR drug resistant cells was determined to be approximately 15 times less than in normal MCF7 cells.

Quantitative RT-PCR was then performed using primers specific either for RAB6 or RAB6C. In both cases, β-actin mRNA was also measured and used to normalize results obtained with MCF7/AdrR drug resistant cells and MCF7 drug sensitive cells. The primers used to amplify RAB6 sequences were 5'-GCTGAGGAAATTCAAGCTGG-3' (SEQ ID NO:35) and 5'-CAACAACTGCCACAGTG-GAGTC-3' (SEQ ID NO:36). The primers used to amplify RAB6C sequences were 5'-GCTGAGGAAAT-TCAAGCTGG-3' (SEQ ID NO:35) and 5'-CTACTA-CAGCTGCAGCAGAATC-3' (SEQ ID NO:37). β-actin sequences were amplified using primers 5'-ACGACATG-GAGAAGATCTGGC-3' (SEQ ID NO:38) and 5'-TTCTC-GATGCTCGACGGGCTACC-3' (SEQ ID NO:39). The amounts of RT-PCR products were quantitatively determined by densitometry. The amount of RAB6 mRNA was reduced about 9-fold in MCF7/AdrR drug resistant cells relative to MCF7 drug sensitive cells. Similarly, the amount of RAB6C mRNA was reduced about 7-fold in MCF7/AdrR cells relative to MCF7 cells.

EXAMPLE 3

Exogenous Expression of WTH3, RAB6C and RAB6

Reversion of MDR phenotype by overexpression of WTH3, RAB6 or RAB6C in MCF7/AdrR cells. WTH3, RAB6 and RAB6C cDNAs were inserted into pcDNA1.1/ Amp expression vectors (Invitrogen Corp.) and transfected into drug resistant MCF7/AdrR cells (Lipofect Amine Plus™; Life Technologies, Inc., (GIBCO)). Expression of the exogenous WTH3 (pcDNA/WTH3), RAB6 (pcDNA/ RAB6) or RAB6C (pcDNA/RAB6C) genes in transfected cells was confirmed by RT-PCR. Control cells were provided by transfection with pcDNA1.1/Amp which contained no insert. Cells were exposed to various concentrations of doxorubicin and viablity was determined after 72 hours by MTT assay. Cells expressing endogenous WTH3 were shown to have increased sensitivity to doxorubicin and vincristine. Cells expressing RAB6 or RAB6C cDNAs were tested for sensitivity to doxorubicin. Mean $IC_{50} \pm$ SD values were 4.93±0.30 μM for control cells, 2.23±0.17 μM for pcDNA/RAB6 containing cells, and 1.53±0.13 μM for pcDNA/RAB6C containing cells. The drug resistant control cells were 3.2 (P<0.0001) times more resistant to the antitumor drug than pcDNA/RAB6C containing cells and 2.2 (P<0.0001) times more resistant to the antitumor drug than pcDNA/RAB6 containing cells.

Doxorubicin Efflux. Retention of doxorubicin was analyzed by flow cytometry in load/chase experiments. Approximately $5 \times 10^4$ cells per well in 6 well dishes were loaded with 30 µg/ml doxorubicin in 1 ml of culture media for 2 hr. at 37° C. The culture media was chases with fresh media containing no doxorubicin. At various times (0, 3, and 5 hr.) following the chase, the media was removed, and the cells were washed twice in PBS and trypsinized. Cells were centrifuged at 1000×g for 5 min. and resuspended in 300 µl of 1% paraformaldehyde. The doxorubicin content was determined by flow cytometry as described by Doyle, et al., *Expression of a 95 kDa membrane protein is associated with low daunorubicin accumulation in leukaemic blast cells*, 71 BR. CANCER J. 52 (1995). Control cells demonstrated a significant loss of fluorescence after 3 hours of chase and a further loss after 5 hours (FIG. 8*a*). In comparison, after 3 hours of chase, both pcDNA/RAB6C (FIG. 8*b*) and pcDNA/RAB6 (FIG. 8*c*) containing cells retained fluorescence and continued to retain fluorescence after 5 hours of chase.

Fluorescence microscopy confirmed retention of doxorubicin by pcDNA/RAB6 and pcDNA/RAB6C containing cells after a 6 hour chase (FIG. 9). Approximately $5 \times 10^4$ MCF7/AdrR cells transfected with pcDNA/RAB6, pcDNA/RAB6C, or pcDNA 1.1/Amp were cultured in 6 well dishes. Cells were loaded with 30 µg/ml doxorubicin in media for 2 hours. The media was removed and the cells were washed with PBS, followed by the addition of fresh media without doxorubicin (chase). Cells were examined for fluorescence at 488 nm at the end of the loading period and after 6 hours of chase). After 6 hours of chase, only cells transfected with RAB6 (FIG. 9H) and RAB6C (FIG. 9J) continued to fluoresce. At this point, control cells (FIG. 9M) showed no fluorescence. The control cells were healthy and continued to divide following the chase. These results are consistent with the increases sensitivity to doxorubicin demonstrated above.

We claim:

1. An isolated nucleic acid which encodes an amino acid sequence comprising SEQ ID NO:12 from about amino acid residue number 1 to about amino acid residue number 254.

2. The isolated nucleic acid of claim 1 which comprises the nucleotides of SEQ ID NO:11.

3. A recombinant DNA comprising the isolated nucleic acid of any one of claims 1 or 2 operably linked to regulatory control sequences which can effect expression of said nucleic acid in a host cell.

4. An isolated expression vector comprising the recombinant DNA of claim 1.

5. An isolated host cell comprising the vector of claim 4.

6. The host cell of claim 5 wherein said host cell is a eukaryotic or a prokaryotic host cell.

7. A method of producing a recombinant wth3 protein which process comprises:
   a) culturing the host cell of claim 5 in a culture medium under conditions suitable for expression of the wth3 protein in said host cell, and
   b) recovering said recombinant protein from said host cell or said culture medium.

8. A wth3 protein prepared by the method of claim 7.

9. A recombinant expression vector suitable for increasing drug sensitivity in an isolated host cell comprising a nucleotide as claimed in claim 1 and a regulatory sequence operatively linked to the nucleic acid.

* * * * *